United States Patent [19]

Murayama et al.

[11] 4,212,974
[45] Jul. 15, 1980

[54] PIPERIDINE DERIVATIVES

[75] Inventors: Keisuke Murayama; Syoji Morimura; Takao Yoshioka; Toshimasa Toda; Eiko Mori; Hideo Horiuchi; Susumu Higashida; Katsuaki Matsui; Tomoyuki Kurumada; Noriyuki Ohta; Hisayou Osawa, all of Hiromachi, Japan

[73] Assignee: Sankyo Co. Ltd., Tokyo, Japan

[21] Appl. No.: 924,665

[22] Filed: Jul. 14, 1978

Related U.S. Application Data

[62] Division of Ser. No. 753,691, Dec. 23, 1976, Pat. No. 4,125,533, which is a division of Ser. No. 553,087, Feb. 26, 1975, Pat. No. 4,016,168, which is a division of Ser. No. 405,570, Oct. 11, 1973, Pat. No. 3,899,464.

[30] Foreign Application Priority Data

Oct. 26, 1972 [JP] Japan .................................. 47-107408

[51] Int. Cl.$^2$ ............................................ C07D 405/04
[52] U.S. Cl. ...................................... 546/19; 544/129; 260/45.8 NZ
[58] Field of Search ........................... 546/19; 544/129

[56] References Cited

U.S. PATENT DOCUMENTS

| | | | |
|---|---|---|---|
| 4,016,168 | 4/1977 | Murayama et al. | 546/19 |
| 4,125,533 | 11/1978 | Murayama et al. | 546/19 |

Primary Examiner—John M. Ford
Assistant Examiner—Robert T. Bond
Attorney, Agent, or Firm—Toren, McGeady and Stanger

[57] ABSTRACT

A novel piperidine derivative having a stabilizing effect on a synthetic polymeric material and a composition comprising said piperidine derivative and a synthetic polymeric material.

10 Claims, No Drawings

PIPERIDINE DERIVATIVES

This is a division of application Ser. No. 753,691, filed on Dec. 23, 1976 now U.S. Pat. No. 4,125,533, which, in turn, was a divisional application of Ser. No. 553,087, now U.S. Pat. No. 4,016,168, filed on Feb. 26, 1975, which, in turn, was a divisional application of Ser. No. 405,570, filed on Oct. 11, 1973, now U.S. Pat. No. 3,899,464.

DETAILED DESCRIPTION OF THE INVENTION

This invention relates to a novel piperidine derivative and use thereof as stabilizer for polymeric materials.

More particularly, the piperidine derivative of this invention has the following formula:

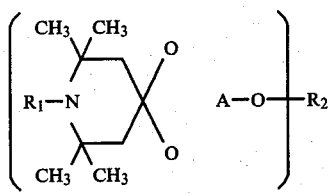

wherein $R_1$ represents hydrogen atom, an alkyl group, a substituted alkyl group, an alkenyl group, an alknyl group, a substituted or unsubstituted aralkyl group, an aliphatic acyl group, an alkoxycarbonyl group or an aralkoxycarbonyl group, n is an integer of 1 to 4; when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group

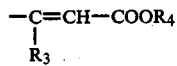

in which $R_3$ represents hydrogen atom, a lower alkyl group or phenyl group and $R_4$ represents an alkyl group; when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid; when n is 3, $R_2$ represents an aromatic triacyl group or a trivalent group from an oxoacid; and when n is 4, $R_2$ represents an aromatic tetraacyl group, and A represents a group

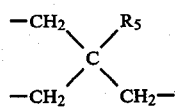

in which $R_5$ represents hydrogen atom or a lower alkyl group or, when n is 1, $R_5$ may represent together with $R_2$ a group

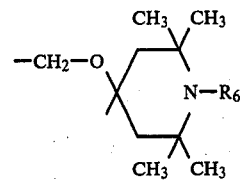

in which $R_6$ represents the same group as defined in $R_1$ and may be the same or different from $R_1$, or a group

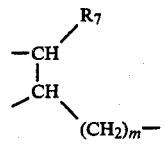

in which n is 1 or 2 and $R_7$ represents hydrogen atom or, when n and m are 1, $R_7$ represents methylene group together with $R_2$.

The inventors of this invention have found that the piperidine derivatives of the above-mentioned formula (I) have a stabilising effect, especially an effectively preventive property from photo- and thermal-deterioration of synthetic polymeric materials such as polyolefin, polyvinyl chloride, polyvinylidene chloride, polyacetal, polyester, polyamide, polyurethane, epoxy resin and the like.

The term "polymeric material" as used herein is intended to embrace polyolefins including
  homopolymers of olefins such as low-density and high-density polyethylene, polypropylene, polystyrene, polybutadiene, polyisoprene and the like, and copolymers of olefins with other ethylenically unsaturated monomers such as ethylene-propylene copolymer, ethylene-butene copolymer, ethylene-vinyl acetate copolymer, styrene-butadiene copolymer, acrylonitrile-styrene-butadiene copolymer and the like;
polyvinyl chlorides and polyvinylidene chlorides including
  homopolymer of each of vinyl chloride and vinylidene chloride, vinyl chloride-vinylidene chloride copolymer and copolymers of each of vinyl chloride and vinylidene chloride with vinyl acetate or other ethylenically unsaturated monomers;
polyacetals such as polyoxymethylene and polyoxyethylene;
polyesters such as polyethylene terephthalate;
polyamides
  such as 6-nylon, 6,6-nylon and 6,10-nylon; and
polyurethanes; and
epoxy resins.

Synthetic polymers have been widely utilized, owing to their excellent properties, in various forms or shapes, for example, filament, fibre, yarn, film, sheet, other molded article, latex and foam.

The present piperidine derivatives of the above-mentioned formula (I), when more separately classified, include those compounds of the following formulae;

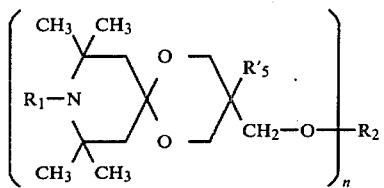

wherein $R_1$, $R_2$ and n are as defined above, and $R'_5$ represents hydrogen atom or a lower alkyl group;

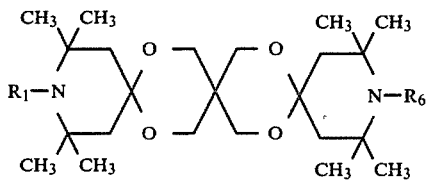

wherein $R_1$ and $R_6$ are as defined above,

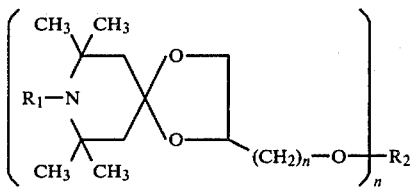

wherein $R_1$, $R_2$, n and m are as defined above, and

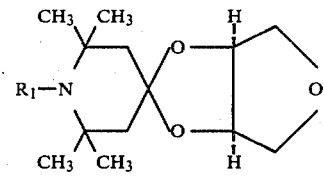

wherein $R_1$ is as defined above.

In the above general formulae (II) to (V), each of $R_1$ and $R_6$ which is referred to in (III) is an alkyl group having carbon atoms of 1-8, for example, methyl, ethyl, propyl, butyl or octyl, preferably an alkyl group having carbon atoms of 1-4, most preferably methyl; a substituted alkyl group having carbon atoms of 1-3 in its alkyl, for example, 2-hydroxyalkyl, e.g., 2-hydroxyethyl, alkoxyalkyl having carbon atoms of 1-4 in its alkoxy, e.g., 2-ethoxyethyl or ethoxymethyl, saturated aliphatic acyl having carbon atoms of 2-18, preferably 2-4, in its acyl, unsaturated aliphatic acyl having carbon atoms of 3-4 or acyloxyalkyl having benzoyl, e.g., 2-acetoxyethyl, 2-stearoyloxyethyl, 2-benzoyloxyethyl or 2-acryloyloxyethyl, and preferably 2-acetoxyethyl, 2-acryloyloxyethyl or 2-benzoyloxyethyl; cyanoalkyl, e.g., 2-cyanoethyl or cyanomethyl, halogenoalkyl, e.g., 2-chloroethyl, epoxyalkyl, e.g., 2,3-epoxypropyl, or alkoxycarbonylalkyl having carbon atoms of 1-4 in its alkoxy, e.g., methoxycarbonylmethyl, ethoxycarbonylmethyl, butoxycarbonylmethyl or 2-methoxycarbonylethyl; an alkenyl group having carbon atoms of 3-4, preferably allyl; an alkynyl group having carbon atoms of 3-4, preferably 2-propynyl; a substituted or unsubstituted aralkyl group, for example, benzyl or halogeno- or methylsubstituted benzyl, preferably benzyl; a saturated or unsaturated aliphatic acyl group having carbon atoms of 2-8, for example acetyl, propionyl, butyryl, acryloyl, methacryloyl or crotonoyl, preferably a saturated aliphatic acyl having carbon atoms of 2-4 or an unsaturated aliphatic acyl having carbon atoms of 3-4, most preferably acetyl; an alkoxycarbonyl group having carbon atoms of 2-5, for example, ethoxycarbonyl or butoxycarbonyl; or an aralkoxycarbonyl group, for example benzyloxycarbonyl. Particularly preferable $R_1$ is hydrogen atom, an alkyl group having carbon atoms of 1-4, allyl group, benzyl group, an alkoxycarbonylmethyl group having carbon atoms of 1-4 in its alkoxy, 2,3-epoxypropyl group, 2-saturated aliphatic acyloxyethyl group having carbon atoms of 2-18 in its acyl or an aliphatic acyl group having carbon atoms of 2-4. Hydrogen atom and methyl group are most preferable.

In the above formulae (II) and (IV), $R_2$ is, when n is 1 an aliphatic monoacyl group such as a saturated aliphatic acyl group having carbon atoms of 1-18, preferably 2-18 in which sulfur atom may be put in the acyl chain or an unsaturated aliphatic acyl group having carbon atoms of 3-6, of which the saturated or unsaturated aliphatic acyl may have phenyl substituted with alkyl having carbon atoms of 1-4 and/or hydroxy or unsubstituted phenyl, for example, formyl, acetyl, propionyl, isobutyryl, octanoyl, lauroyl, stearoyl, acryloyl, methacryloyl, phenylacetyl, 3-(3,5-di-t-butyl-4-hydroxyphenyl)propionyl, sorboyl, cinnamoyl or 3-octylthiopropionyl and preferably saturated aliphatic acyl having carbon atoms of 2-18, most preferably 8-18, or an aromatic monoacyl group, for example, benzoyl which may be substituted with alkyl or alkoxy having carbon atoms of 1-4, halogen or hydroxy, e.g., benzoyl, o-, m- or p-toluoyl, p-t-butylbenzoyl, o-, m- or p-chlorobenzoyl, salicyloyl or o-, m- or p-anisoyl, or $\alpha$- or $\beta$-naphthoyl, preferably benzoyl which may be substituted with alkyl having carbon atoms of 1-4 or hydroxy, or a heterocyclic monoacyl group, for example, 2-furoyl, isonicotinoyl, nicotinoyl or morpholincarbonyl; an alkyl group having carbon atoms of 1-18, for example, methyl, ethyl, propyl, butyl, hexyl, heptyl, octyl, dodecyl or stearoyl; an alkenyl group having carbon atoms of 3-4, preferably allyl; an alkynyl group having carbon atoms of 3-4, preferably 2-propynyl; an aralkyl group having carbon atoms of 7-8, preferably benzyl; an aryl group having carbon atoms of 6-11, for example, phenyl o-, m- or p-tolyl or $\alpha$- or $\beta$-naphthyl; an alkoxyalkyl group having carbon atoms of 1-4, preferably 1-2, in its alkoxy and its alkyl respectively, for example, methoxymethyl or ethoxymethyl; an epoxyalkyl group, preferably 2,3-epoxypropyl; an alkoxysulfonylalkyl group having carbon atoms of 1-4 in its alkoxy and its alkyl respectively, for example, 3-methoxysulfonylpropyl; a N-substituted carbamoyl group or a N-substituted thiocarbamoyl group having a substituent, for example, alkyl having carbon atoms of 1-4, e.g., methyl, ethyl or butyl, aryl, e.g., phenyl or cycloalkyl, e.g., cyclohexyl, preferably a carbamoyl group substituted with ethyl, phenyl or cyclohexyl, a monovalent group from an oxoacid, such as, a group derived from an oxoacid, e.g., substituted or unsubstituted sulfinic acid, sulfonic acid, phosphoric acid, phosphorous acid of phosphonic acid by removing one hydroxyl group and examples of the oxoacid are benzenesulfinic acid, benzenesulfonic acid, p-toluenesulfonic acid, methanesulfonic acid, diphenylphosphonic acid, dialkylphosphoric acid of $C_1$-$C_8$ or diphenylphosphorous acid, dialkylphosphorous acid of $C_1-C_8$, or a group

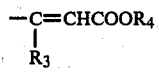

wherein $R_3$ represents a lower alkyl group having carbon atoms of 1-4, preferably methyl and $R_4$ represents an alkyl group having carbon atoms of 1-8, for example, 2-ethoxycarbonylvinyl, 1-methyl-2-methoxycarbonylvinyl, 1-methyl-2-octoxycarbonylvinyl or 1-phenyl-2-ethoxycarbonylvinyl.

When n is 2, $R_2$ is a diacyl group such as a saturated aliphatic diacyl having carbon atoms of 2-18, in which sulfur atom may be put in the acyl chain or an unsaturated aliphatic acyl group having carbon atoms of 4-6, preferably a saturated aliphatic diacyl having carbon atoms of 4-12, e.g., oxalyl, malonyl, succinyl, adipoyl, suberoyl, sebacoyl, thiodipropionyl or fumaryl, an aromatic diacyl having 8 carbon atoms, e.g., terephthaloyl or isophthaloyl preferably terephthaloyl; an alkylene group having carbon atoms of 2-6, for example, ethylene, propylene, butylene or hexamethylene; an alkenylene group having carbon atoms of 4-6, for example, 2-butenylene; an aralkylene group having carbon atoms of 8-10, for example, p-xylylene; a N-substituted dicarbamoyl group having a substituent, for example, alkylene having carbon atoms of 2-6, e.g., ethylene, propylene, butylene or hexamethylene, or arylene having carbon atoms of 6-7, e.g., p-phenylene or 2,4-tolylene, or p,p'-methanediphenylene, a divalent group from an oxoacid, e.g., sulfurous acid, sulfuric acid, substituted or unsubstituted sulfinic acid, sulfonic acid, phosphoric acid or phosphorous acid by removing two hydroxyl groups and examples of the oxoacid are sulfurous acid, sulfuric acid, phenylphosphorous acid.

When n is 3, $R_2$ is an aromatic triacyl having 9 carbon atoms, for example, trimellitoyl or trimesoyl; or a trivalent group from an oxoacid, e.g., phosphoric acid, phosphorous acid or boric acid by removing three hydroxyl groups, for example,

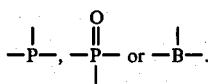

When n is 4, $R_2$ is an aromatic tetraacyl group having 10 carbon atoms, for example

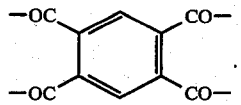

Particularly preferable $R_2$ is a saturated aliphatic acyl group having carbon atoms of 2-18, benzoyl group which may be substituted with alkyl of $C_1-C_4$ or hydroxy, an alkyl group having carbon atoms of 1-18, an allyl group, 2,3-epoxypropyl group, a saturated aliphatic diacyl group having carbon atoms of 4-12, or terephthaloyl group. The lower alkyl group of R's in the formula (II) has preferably carbon atoms of 1-3 and is exemplified by methyl, ethyl or propyl, preferably methyl or ethyl. In the formula (II), n is preferred to be 1 or 2. In the formula (IV), n and m are preferred to be 1-2 and 1 respectively.

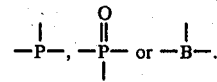

Representatives of the piperidine derivatives (I) of this invention are illustrated hereunder. However, these illustrated compounds are not intended to limit this invention.

The compounds of the formula (II).

(II-1) 9-Aza-3-hydroxymethyl-8,8,9,10,10-pentamethyl-1,5-dioxa-spiro[5.5] undecane (II-2) 9-Aza-3-hydroxymethyl-3,8,8,10,10-pentamethyl-1,5-dioxa-spiro[5.5] undecane (II-3) 3-Acetoxymethyl-9-aza-3,8,8,10,10-pentamethyl-1,5-dioxa-spiro[5.5]undecane (II-4) 9-Aza-3-hydroxymethyl-3,8,8,9,10,10-hexamethyl-1,5-dioxa-spiro[5.5]undecane (II-5) 3-Acetoxymethyl-9-aza-3,8,8,9,10,10-hexamethyl-1,5-dioxa-spiro[5.5]undecane (II-6) 9-Aza-3-hydroxymethyl)-3,8,8,10,10-pentamethyl-9-octyl-1,5-dioxa-spiro[5.5]undecane (II-7) 3-Acryloyloxymethyl-9-aza-3,8,8,10,10-pentamethyl-1,5-dioxa-spiro[5.5]undecane (II-8) 9-Aza-3-benzoyloxymethyl-3,8,8,10,10-pentamethyl-1,5-dioxa-spiro[5.5]undecane (II-9) 9-Aza-3-benzoyloxymethyl-3,8,8,9,10,10-hexamethyl-1,5-dioxa-spiro[5.5]undecane (II-10) 9-Aza-3,8,8,9,10,10-hexamethyl-1,5-dioxa-3-stearoyloxymethyl-spiro[5.5]undecane (II-11) 3-Acetoxymethyl-9-allyl-9-aza-3,8,8,10,10-pentamethyl-1,5-dioxa-spiro[5.5]undecane (II-12) 3-Acetoxymethyl-9-aza-3,8,8,10,10-pentamethyl-1,5-dioxa-9-(2-propynyl)-spiro[5.5]undecane (II-13) 3-Acetoxymethyl-9-aza-9-cyanomethyl-3,8,8,10,10-pentamethyl-1,5-dioxa-spiro[5.5]undecane (II-14) 9-Aza-3-(2,3-epoxypropyloxymethyl)-3,8,8,9,10,10-hexamethyl-1,5-dioxa-spiro[5.5]undecane (II-15) 3-Acetoxymethyl-9-aza-9-(2,3-epoxypropyl)-3,8,8,10,10-pentamethyl-1,5-dioxa-spiro[5.5]undecane (II-16) 3-Acetoxymethyl-9-aza-9-(2-hydroxyethyl)-3,8,8,10,10-pentamethyl-1,5-dioxa-spiro[5.5]undecane (II-17) 9-(2-Acetoxyethyl)-3-acetoxymethyl-9-aza-3,8,8,10,10-pentamethyl-1,5-dioxa-spiro[5.5]undecane (II-18) 3-Acetoxymethyl-9-asa-9-ethoxymethyl-3,8,8,10,10-pentamethyl-1,5-dioxa-spiro[5.5]undecane (II-19) 9-Acryloyl-3-acryloyloxymethyl-9-aza-3,8,8,10,10-pentamethyl-1,5-dioxa-spiro[5.5]undecane (II-20) 9-Aza-9-(p-chlorobenzyl)-3-hydroxymethyl-3,8,8,10,10-pentamethyl-1,5-dioxa-spiro[5.5]undecane (II-21) 9-Aza-3-ethyl-3-hydroxymethyl-8,8,10,10-tetramethyl-1,5-dioxa-spiro[5.5]undecane (II-22) 9-Aza-3-ethyl-3-hydroxymethyl-8,8,10,10-tetramethyl-9(p-methylbenzyl)-1,5-dioxa-spiro[5.5]undecane (II-23) 3-Acetoxymethyl-9-aza-3-ethyl-9-ethoxycarbonylmethyl-8,8,10,10-tetramethyl-1,5-dioxaspiro[5.5]undecane
(II-24) 9-Aza-3-ethyl-8,8,9,10,10-pentamethyl-3-(β-octylthiopropionyloxymethyl)-1,5-dioxa-spiro[5.5]undecane
(II-25) 3-Acetoxymethyl-9-aza-3-ethyl-8,8,10,10-tetramethyl-1,5-dioxa-spiro[5.5]undecane
(II-26) 3-Acetoxymethyl-9-aza-3-ethyl-8,8,9,10,10-pentamethyl-1,5-dioxa-spiro[5.5]undecane
(II-27) 3-Acryloyloxymethyl-9-aza-3-ethyl-8,8,9,10,10-pentamethyl-1,5-dioxa-spiro[5.5]undecane
(II-28) 9-Aza-3-ethyl-8,8,9,10,10-pentamethyl-1,5-dioxa-3-stearoyloxymethyl-spiro[5.5]undecane
(II-29) 3-Acetoxymethyl-9-aza-9-butoxycarbonyl-3,8,8,10,10-pentamethyl-1,5-dioxa-spiro[5.5]undecane
(II-30) 3-Acetoxymethyl-9-aza-9-benzyloxycarbonyl-3,8,8,10,10-pentamethyl-1,5-dioxa-spiro[5.5]-undecane
(II-31) 9-Aza-3-(p-t-butylbenzoyloxymethyl)-3-ethyl-8,8,9,10,10-pentamethyl-1,5-dioxa-spiro[5.5]undecane
(II-32) 9-Aza-3,8,8,9,10,10-hexamethyl-1,5-dioxa-3-salicyloyloxymethyl-spiro[5.5]undecane
(II-33) 9-Aza-3-ethyl-8,8,9,10,10-pentamethyl-1,5-dioxa-3-salicyloyloxymethyl-spiro[5.5]undecane
(II-34) 9-Aza-3-ethyl-8,8,9,10,10-pentamethyl-3-β-naphthoyloxymethyl-1,5-dioxa-spiro[5.5]undecane
(II-35) 9-Aza-3-(2-furoyloxymethyl)-3,8,8,9,10,10-hexamethyl-1,5-dioxa-spiro[5.5]undecane
(II-36) 9-Aza-3,8,8,9,10,10-hexamethyl-3-nicotinoyloxymethyl-1,5-dioxa-spiro[5.5]undecane
(II-37) 9-Aza-3-benzenesulfinyloxymethyl-3,8,8,9,10,10-hexamethyl-1,5-dioxa-spiro[5.5]undecane
(II-38) 9-Aza-3-mezyloxymethyl-3,8,8,9,10,10-hexamethyl-1,5-dioxa-spiro[5.5]undecane
(II-39) 9-Aza-3,8,8,9,10,10-hexamethyl-1,5-dioxa-3-tosyloxymethyl-spiro[5.5]undecane
(II-40) 9-Aza-3-hydroxymethyl-3,8,8,10,10-pentamethyl-9-iodomethyl-1,5-dioxa-spiro[5.5]undecane
(II-41) 9-Aza-3-[β-(3,5-di-t-butyl-4-hydroxyphenyl)-propionyloxymethyl]-3,8,8,9,10,10-hexamethyl-1,5-dioxa-spiro[5.5]undecane
(II-42) 9-Aza-3-(3-methoxysulfonylpropyloxymethyl)-3,8,8,9,10,10-hexamethyl-1,5-dioxa-spiro[5.5]undecane
(II-43) 9-Aza-3-ethyl-3-ethylcarbamoyloxymethyl-8,8,9,10,10-pentamethyl-1,5-dioxa-spiro[5.5]undecane
(II-44) 9-Aza-3-ethyl-8,8,9,10,10-pentamethyl-1,5-dioxa-3-phenylcarbamoyloxymethyl-spiro[5.5]undecane
(II-45) 9-Aza-3-cyclohexylthiocarbamoyloxymethyl-3-ethyl-8,8,9,10,10-pentamethyl-1,5-dioxa-spiro[5.5]undecane
(II-46) 9-Aza-3,8,8,9,10,10-hexamethyl-3-octyloxymethyl-1,5-dioxa-spiro[5.5]undecane
(II-47) 9-Aza-3,8,8,9,10,10-hexamethyl-1,5-dioxa-3-stearyloxymethyl-spiro[5.5]undecane
(II-48) 3-Allyloxymethyl-9-aza-3,8,8,9,10,10-hexamethyl-1,5-dioxa-spiro[5.5]undecane
(II-49) 9-Aza-3,8,8,9,10,10-hexamethyl-1,5-dioxa-3-(2-prepynyloxymethyl)-spiro[5.5]undecane
(II-50) 9-Aza-3-benzyloxymethyl-3,8,8,9,10,10-hexamethyl-1,5-dioxa-spiro[5.5]undecane
(II-51) 9-Aza-3-ethoxymethoxymethyl-3,8,8,10,10-pentamethyl-1,5-dioxa-spiro[5.5]undecane
(II-52) 9Aza-3-(β-ethoxycarbonylvinyloxymethyl)-3-ethyl-8,8,9,10,10-pentamethyl-1,5-dioxa-spiro[5.5]undecane
(II-53) 9-Aza-3-(α-methyl-β-methoxycarbonylvinyloxymethyl)-3,8,8,9,10,10-hexamethyl-1,5-dioxa-spiro[5.5]undecane
(II-54) 9-Aza-3,8,8,9,10,10-hexamethyl-1,5-dioxa-3-phenoxymethyl-spiro[5.5]undecane
(II-55) Bis(9-aza-3-ethyl-8,8,9,10,10-pentamethyl-1,5-dioxa-spiro[5.5]-3-undecylmethyl)carbonate
(II-56) Bis(9-aza-3,8,8,10,10-pentamethyl-1,5-dioxa-spiro[5.5]-3-undecylmethyl)adipate
(II-57) Bis(9-aza-3,8,8,9,10,10-hexamethyl-1,5-dioxa-spiro[5.5]-3-undecylmethyl)adipate
(II-58) Bis(9-aza-3-ethyl-8,8,9,10,10-pentamethyl-1,5-dioxa-spiro[5.5]-3-undecylmethyl)sebacate
(II-59) Bis(9-aza-3,8,8,10,10-pentamethyl-1,5-dioxa-spiro[5.5]-3-undecylmethyl)terephthalate
(II-60) Bis(9-aza-3,8,8,9,10,10-hexamethyl-1,5-dioxa-spiro[5.5]-3-undecylmethyl)terephthalate
(II-61) Bis(9-aza-3-ethyl-8,8,9,10,10-pentamethyl-1,5-dioxa-spiro[5.5]-3-undecylmethyl)thiodipropionate
(II-62) Bis(9-aza-3-ethyl-8,8,9,10,10-pentamethyl-1,5-dioxa-spiro[5.5]-3-undecylmethyl)sulfite
(II-63) 1,2-Bis(9-aza-3,8,8,9,10,10-hexamethyl-1,5-dioxa-spiro[5.5]-3-undecylmethoxy)ethane
(II-64) 1,4-Bis(9-aza-3-ethyl-8,8,9,10,10-pentamethyl-1,5-dioxa-spiro[5.5]-3-undecylmethoxy)-2-butene
(II-65) α,α'-Bis(9-aza-3,8,8,9,10,10hexamethyl-1,5-dioxa-spiro[5.5]-3-undecylmethoxy)-p-xylene
(II-66) Bis(9-aza-3-ethyl-8,8,9,10,10-pentamethyl-1,5-dioxa-spiro[5.5]-3-undecylmethyl)hexamethylene-1,6-dicarbamate
(II-67) Bis(9-aza-3-ethyl-8,8,9,10,10-pentamethyl-1,5-dioxa-spiro[5.5]-3-undecylmethyl)tolylene-2,4-dicarbamate
(II-68) Bis(9-aza-3-ethyl-8,8,9,10,10-pentamethyl-1,5-dioxa-spiro[5.5]-3-undecylmethyl)diphenylmethane-p,p'-dicarbamate
(II-69) Tris(9-aza-3-ethyl-8,8,9,10,10-pentamethyl-1,5-dioxa-spiro[5.5]-3-undecylmethyl)trimesate
(II-70) Tris(9-aza-3-ethyl-8,8,9,10,10-pentamethyl-1,5-dioxa-spiro[5.5]-3-undecylmethyl)phosphite
(II-71) Tetrakis(9-aza-3-ethyl-8,8,9,10,10-pentamethyl-1,5-dioxa-spiro[5.5]-3-undecylmethyl)pyromellitate
(II-72) 9-Aza-9-benzyl-3-ethyl-3-hydroxymethyl-8,8,10,10-tetramethyl-1,5-dioxa-spiro[5.5]undecane
(II-73) 3-Acetoxymethyl-9-aza-9-benzyl-3-ethyl-8,8,10,10-tetramethyl-1,5-dioxa-spiro[5.5]undecane
(II-74) 3-Acetoxymethyl-9-aza-3-ethyl-9-methoxycarbonylmethyl-8,8,10,10-tetramethyl-1,5-dioxa-spiro[5.5]undecane
(II-75) 9-Aza-3-ethyl-3-stearoyloxymethyl-8,8,10,10-tetramethyl-1,5-dioxa-spiro[5.5]undecane
(II-76) 9-Aza-3-benzoyloxymethyl-3-ethyl-8,8,10,10-tetramethyl-1,5-dioxa-spiro[5.5]undecane
(II-77) 9-Aza-3-benzoyloxymethyl-3-ethyl-8,8,9,10,10-pentamethyl-1,5-dioxa-spiro[5.5]undecane
(II-78) 9-Aza-3-ethyl-3-salicyloyloxymethyl-8,8,10,10-tetramethyl-1,5-dioxa-spiro[5.5]undecane
(II-79) Bis[9-aza-3-ethyl-8,8,10,10-tetramethyl-1,5-dioxa-spiro[5.5]-3-undecylmethyl]adipate (II-80) Bis[9-aza-3-ethyl-8,8,9,10,10-pentamethyl-1,5-dioxa-spiro[5.5]-3-undecylmethyl]adipate (II-81) Bis[9-aza-3-ethyl-8,8,10,10-tetramethyl-1,5-dioxa-spiro[5.5]-3-undecylmethyl]terephthalate (II-82) Bis[9-aza-3-ethyl-8,8,9,10,10-pentamethyl-1,5-dioxa-spiro[5.5]-3-undecylmethyl]terephthalate The compounds of the formula (III).

(III-1) 2,2,6,6-Tetramethylpiperidine-4-spiro-2'-(1',3'-dioxane)-5'-spiro5"-(1",3"-dioxane)-2"-spiro4"'-(2"',2"',6"',6"'-tetramethylpiperidine)

(III-2) 1,2,2,6,6-Pentamethylpiporidine-4-spiro-2'-(1',3'-dioxane)-5'-spiro5"-(1",3"-dioxane)-2"-spiro-4"'-(1"',2"',2"',6"',6"'-pentamethylpiperidine)

(III-3) 2,2,6,6-Tetramethyl-1-octylpiperidine-4-spiro-2'-(1',3'-dioxane)-5'-spiro5"-(1",3"-dioxane)-2"-spiro-4"'-(2"',2"',6"',6"'-tetramethylpiperidine)

(III-4) 2,2,6,6-Tetramethyl-1-octylpiperidine-4-spiro-2'-(1',3'-dioxane)-5'-spiro5"-(1",3"-dioxane)-2"-spiro-4"'-(2"',2"',6"',6"'-tetramethyl-1"'-octylpiperidine)

(III-5) 1-Allyl-2,2,6,6-tetramethylpiperidine-4-spiro-2'-(1',3'-dioxane)-5'-spiro5"-(1",3"-dioxane)-2"-spiro-4"'-(1"'-allyl-2"',2"',6"',6"'-tetramethylpiperidine)

(III-6) 1-Ethoxycarbonylmethyl-2,2,6,6-tetramethylpiperidine-4-spiro-2'-(1',3'-dioxane)-5'-spiro-5'-(1",3"-dioxane)-2"-spiro-4"'-(1"'-ethoxycarbonylmethyl-2∝",2"',6"',6"'-tetramethylpiperidine)

(III-7) 1-Benzyl-2,2,6,6-tetramethylpiperidine-4-spiro-2'-(1',3'-dioxane)-5'-spiro5"-(1",3"-dioxane)-2"-spiro-4"'-(1"'-benzyl-2"',2"',6"',6"'-tetramethylpiperidine)

(III-8) 1-(2-Hydroxyethyl)-2,2,6,6-tetramethylpiperidine-4-spiro2'-(1',3'-dioxane)-5'-spiro-5"-(1",3"-dioxane)-2"-spiro-4"'-[1"'-(2-hydroxyethyl)-2"',2"',6"',6"'-tetramethylpiperidine]

(III-9) 1-(2-Acetoxyethyl)-2,2,6,6-tetranothylpiperidine-4-spiro-2'-(1',5'-dioxane)-5'-spiro-5"-(1",3"-dioxane)-2"-spiro-4"'-[1"'-(2-acetoxyethyl)-2"',2"',6"',6"'-tetramethylpiperidine]

(III-10) 1-(2-Acryloyloxyethyl)-2,2,6,6-tetramethylpiperidine-4-spiro-2'-(1',3'-dioxane)-5'-spiro-5"-(1",3"-dioxane)-2"-spiro-4"'-[1"'-(2-acryloyloxyethyl)-2"',2"',6"',6"'-tetramethylpiperidine]

(III-11) 1-(2-Benzoyloxyethyl)-2,2,6,6-tetramethylpiperidine-4-spiro-2'-(1',3'-dioxane)-5'-spiro5"-(1",3"-dioxane)-2"-spiro-4"'-[1"'-(2'-benzoyloxyethyl)-2"',2"',6"',6"'-tetramethylpiperidine]

(III-12) 1-(2,3-Epoxypropyl)-2,2,6,6-tetramethylpiperidine-4-spiro-2'-(1',3'-dioxane)-5'-spiro-5"-(1",3"-dioxane)-2"-spiro-4"'-[1"'-(2,3-epoxypropyl)-2"',2"',6"',6"'-tetramethylpiperidine]

(III-13) 2,2,6,6-Tetramethyl-1-(2-stearoyloxyethyl)piperidine-4-spiro-2'-(1',3'-dioxane)-5'-spiro-5"-(1",3"-dioxane)-2"-spiro-4"'-[2"',2"',6"',6"'-tetramethyl-1"'-(2-stearoyloxyethyl)piperidine]

(III-14) 2,2,6,6-Tetramethyl-1-methoxycarbonylmethylpiperidine-4-spiro-2'-(1',3'-dioxane)-5'-spiro-5"-(1",3"-dioxane)-2"-spiro-4"'-(2"',2"',6"',6"'-tetramethyl-1"'-methoxycarbonylmethylpiperidine)

The compounds of the formula (IV).

(IV-1) 8-Aza-2-hydroxymethyl-7,7,9,9-tetramethyl-1,4-dioxa-spiro[4.5]decane (IV-2) 8-Aza-2-hydroxymethyl-7,7,8,9,9-pentamethyl-1,4-dioxa-spiro[4.5]decane (IV-3) 8-Aza-2-hydroxyethyl-7,7,9,9-tetramethyl-8-octyl-1,4-dioxa-spiro[4.5]decane (IV-4) 8-Aza-8-(2-hydroxyethyl)-2-hydroxymethyl-7,7,9,9-tetramethyl-1,4-dioxa-spiro[4.5]decane (IV-5) 8-Aza-8-benzyl-2-hydroxymethyl-7,7,9,9-tetramethyl-1,4-dioxa-spiro[4.5]decane (IV-6) 8-Aza-2-(2-hydroxyethyl)-7,7,9,9-tetramethyl-1,4-dioxa-spiro[4.5]decane (IV-7) 8-Aza-2-(2-hydroxyethyl)-7,7,8,9,9-pentamethyl-1,4-dioxa-spiro[4.5]decane (IV-8) 2-Acetoxymethyl-8-aza-7,7,9,9-tetramethyl-1,4-dioxa-spiro[4.5]decane (IV-9) 2-Acetoxymethyl-8-aza-7,7,8,9,9-pentamethyl-1,4-dioxa-spiro[4.5]decane (IV-10) 8-Acetyl-8-aza-2-hydroxymethyl-7,7,9,9-tetramethyl-1,4-dioxa-spiro[4.5]decane (IV-11) 2-Acetoxymethyl-8-acetyl-8-aza-7,7,9,9-tetramethyl-1,4-dioxa-spiro[4.5]decane (IV-12) 2-Acetoxymethyl-8-acryloyl-8-aza-7,7,9,9-tetramethyl-1,4-dioxa-spiro[4.5]decane (IV-13) 2-Acetoxymethyl-8-aza-7,7,9,9-tetramethyl-8-octyl-1,4-dioxa-spiro[4.5]decane (IV-14) 2-Acetoxymethyl-8-allyl-8-aza-7,7,9,9-tetramethyl-1,4-dioxa-spiro[4.5]decane (IV-15) 2-Acetoxymethyl-8-aza-7,7,9,9-tetramethyl-1,4-dioxa-8-(2-propynyl)-spiro[4.5]decane (IV-16) 2-Acetoxymethyl-8-aza-8-benzyl-7,7,9,9-tetramethyl-1,4-dioxa-spiro[4.5]decane (IV-17) 2-Acetoxymethyl-8-aza-8-ethoxycarbonylmethyl-7,7,9,9-tetramethyl-1,4-dioxa-spiro[4.5]decane (IV-18) 2-Acetoxymethyl-8-aza-8-ethoxymethyl-7,7,9,9-tetramethyl-1,4-dioxa-spiro[4.5]decane (IV-19) 2-Acetoxymethyl-8-aza-8-(2,3-epoxypropyl)-7,7,9,9-tetramethyl-1,4-dioxa-spiro[4.5]decane (IV-20) 8-Aza-2-(2,3-epoxypropyloxymethyl)-7,7,9,9-tetramethyl-1,4-dioxa-spiro[4.5]decane (IV-21) 2-Acetoxymethyl-8-aza-8-ethoxycarbonyl-7,7,9,9-tetramethyl-1,4-dioxa-spiro[4.5]decane (IV-22) 2-Acetoxymethyl-8-aza-8-benzyloxycarbonyl-7,7,9,9-tetramethyl-1,4-dioxa-spiro[4.5]decane (IV-23) 2-Acetoxymethyl-8-aza-8-(2-chloroethyl)-7,7,9,9-tetramethyl-1,4-dioxa-spiro[4.5]decane (IV-24) 2-Acetoxymethyl-8-aza-8-(2-hydroxyethyl)-7,7,9,9-tetramethyl-1,4-dioxa-spiro[4.5]decane (IV-25) 2-Acetoxymethyl-8-(2-acetoxyethyl)-8-aza-7,7,9,9-tetramethyl-1,4-dioxa-spiro[4.5]decane (IV-26) 2-Acetoxymethyl-8-aza-8-cyanomethyl-7,7,9,9,tetramethyl-1,4-dioxa-spiro[4.5]decane (IV-27) 8-Aza-2-butyryloxymethyl-7,7,9,9-tetramethyl-1,4-dioxa-spiro[4.5]decane (IV-28) 8-Aza-2-decanoyloxymethyl-7,7,9,9-tetramethyl-1,4-dioxa-spiro[4.5]decane (IV-29) 8-Aza-7,7,8,9,9-pentamethyl-1,4-dioxa-2-stearoyloxymethyl-spiro[4.5]decane (IV-30) 8-Acryloyl-2-acryloyloxymethyl-8-aza-7,7,9,9-tetramethyl-1,4-dioxa-spiro[4.5]decane (IV-31) 2-Acryloyloxymethyl-8-aza-7,7,8,9,9-pentamethyl-1,4-dioxa-spiro[4.5]decane (IV-32) 8-Aza-2-methacryloyloxymethyl-7,7,8,9,9-pentamethyl-1,4-dioxa-spiro[4.5]decane (IV-33) 8-Aza-2-crotonoyl-1,4-dioxa-7,7,8,9,9-pentamethyloxymethyl-spiro[4.5]decane (IV-34) 8-Aza-2-benzoyloxymethyl-7,7,9,9-tetramethyl-1,4-dioxa-spiro[4.5]decane (IV-35) 8-Aza-2-benzoyloxymethyl-7,7,8,9,9-pentamethyl-1,4-dioxa-spiro[4.5]decane
(IV-37) 8-Aza-8-(2-benzoyloxyethyl)-2-benzoyloxymethyl-7,7,9,9-tetramethyl-1,4-dioxa-spiro[4.5]decane
(IV-38) 8-Aza-2-(p-t-butylbenzoyloxymethyl)-7,7,8,9,9-pentamethyl-1,4-dioxa-spiro[4.5]decane
(IV-39) 8-Aza-2-[β-(3,5-di-t-butyl-4-hydroxyphenyl)propionyloxymethyl]-7,7,8,9,9-pentamethyl-1,4-dioxa-spiro[4.5]decane
(IV-40) 8-Aza-7,7,8,9,9-pentamethyl-1,4-dioxa-2-salicyloyloxymethyl-spiro[4.5]decane
(IV-41) 8-Aza-8-benzyl-7,7,9,9-tetramethyl-2-(m-toluoyloxymethyl)-1,4-dioxa-spiro[4.5]decane
(IV-42) 8-Aza-2-(p-chlorobenzoyloxymethyl)-7,7,9,9-tetramethyl-1,4-dioxa-spiro[4.5]decane
(IV-43) 8-Aza-2-(p-chlorobenzoyloxymethyl)-7,7,9,9-tetramethyl-2,4-dioxa-8-(2-propynyl)-spiro[4.5]decane
(IV-44) 2-(o-Anisoyloxymethyl)-8-aza-7,7,9,9-tetramethyl-1,4-dioxa-spiro[4.5]decane
(IV-45) 2-(o-Anisolyloxymethyl)-8-aza-7,7,8,9,9-pentamethyl-1,4-dioxa-spiro[4.5]decane
(IV-46) 8-Aza-7,7,8,9,9-pentamethyl-2-(β-naphthoyloxymethyl)-1,4-dioxa-spiro[4.5]decane
(IV-47) 8-Aza-7,7,8,9,9-pentamethyl-2-(β-octylthiopropionyloxymethyl)-1,4-dioxa-spiro[4.5]decane
(IV-48) 8-Aza-2-(2-furoyloxymethyl)-7,7,8,9,9-pentamethyl-1,4-dioxa-spiro[4.5]decane
(IV-49) 8-Aza-2-isonicotinoyloxymethyl-7,7,8,9,9-pentamethyl-1,4-dioxa-spiro[4.5]decane
(IV-50) 8-Aza-2-benzenesulfinyloxymethyl-7,7,8,9,9-pentamethyl-1,4-dioxa-spiro[4.5]decane
(IV-51) 8-Aza-2-mesyloxymethyl-7,7,8,9,9-pentamethyl-1,4-dioxa-spiro[4.5]decane
(IV-52) 8-Aza-7,7,8,9,9-pentamethyl-1,4-dioxa-2-tosyloxymethyl-spiro[4.5]decane
(IV-53) 8-Aza-2-ethylcarbamoyloxymethyl-7,7,8,9,9-pentamethyl-1,4-dioxa-spiro[4.5]decane
(IV-54) 8-Aza-7,7,8,9,9-pentamethyl-1,4-dioxa-2-phenylcarbamoyloxymethyl-spiro[4.5]decane
(IV-55) 8-Aza-2-cyclohexylthiocarbamoyloxymethyl-7,7,8,9,9-pentamethyl-1,4-dioxa-spiro[4.5]decane
(IV-56) 8-Aza-2-methoxymethyl-7,7,9,9-tetramethyl-1,4-dioxa-spiro[4.5]decane
(IV-57) 8-Aza-7,7,8,9,9-pentamethyl-1,4-dioxa-2-octyloxymethyl-spiro[4.5]decane
(IV-58) 8-Aza-7,7,8,9,9-pentamethyl-1,4-dioxa-2-stearyloxymethyl-spiro[4.5]decane
(IV-59) 2-Allyloxymethyl-8-aza-7,7,9,9-tetramethyl-1,4-dioxa-spiro[4.5]decane
(IV-60) 2-Allyloxymethyl-8-aza-7,7,8,9,9-pentamethyl-1,4-dioxa-spiro[4.5]decane
(IV-61) 8-Aza-7,7,8,9,9-pentamethyl-1,4-dioxa-2-(2-propynyloxymethyl)-spiro[4.5]decane
(IV-62) 8-Aza-2-benzyloxymethyl-7,7,9,9-tetramethyl-1,4-dioxa-spiro[4.5]decane
(IV-63) 8-Aza-2-ethoxymethoxymethyl-7,7,8,9,9-pentamethyl-1,4-dioxa-spiro[4.5]decane
(IV-64) 8-Aza-2-(β-ethoxycarbonylvinyloxymethyl)-7,7,8,9,9-pentamethyl-1,4-dioxa-spiro[4.5]decane
(IV-65) 8-Aza-2-(α-methyl-β-methoxycarbonylvinyloxymethyl)-7,7,8,9,9-pentamethyl-1,4-dioxa-spiro[4.5]decane
(IV-66) 8-Aza-7,7,8,9,9-pentamethyl-2-(α-methyl-β-octyloxycarbonylvinyloxymethyl)-1,4-dioxa-spiro[4.5]decane
(IV-67) 8-Aza-7,7,8,9,9-pentamethyl-1,4-dioxa-2-phenoxymethylspiro[4.5]decane
(IV-68) 8-Aza-2-(2,3-epoxypropyloxymethyl)-7,7,8,9,9-pentamethyl-1,4-dioxa-spiro[4.5]decane
(IV-69) 8-Aza-2-(3-methoxysulfonylpropyloxymethyl)-7,7,8,9,9-pentamethyl-1,4-dioxa-spiro[4.5]decane
(IV-70) Bis(8-aza-7,7,8,9,9-pentamethyl-1,4-dioxaspiro[4.5]-2-decylmethyl)carbonate
(IV-71) Bis(8-aza-7,7,9,9-tetramethyl-1,4-dioxaspiro[4.5]-2-decylmethyl)succinate
(IV-72) Bis(8-aza-7,7,9,9-tetramethyl-1,4-dioxaspiro[4.5]-2-decylmethyl)adipate
(IV-73) Bis(8-aza-7,7,8,9,9-pentamethyl-1,4-dioxaspiro[4.5]-2-decylmethyl)adipate
(IV-74) Bis(8-aza-7,7,9,9-tetramethyl-1,4-dioxaspiro[4.5]-2-decylmethyl)sebacate
(IV-75) Bis(8-aza-7,7,8,9,9-pentamethyl-1,4-dioxaspiro[4.5]-2-decylmethyl)sebacate
(IV-76) Bis(8-aza-7,7,9,9-tetramethyl-1,4-dioxaspiro[4.5]-2-decylmethyl)terephthalate
(IV-77) Bis(8-aza-7,7,8,9,9-pentamethyl-1,4-dioxaspiro[4.5]-2-decylmethyl)terephthalate
(IV-78) Bis(8-aza-7,7,8,9,9-pentamethyl-1,4-dioxaspiro[4.5]-2-decylmethyl)thiopropionate
(IV-79) Bis(8-aza-7,7,8,9,9-pentamethyl-1,4-dioxaspiro[4.5]-2-decylmethyl)sulfite
(IV-80) 1,2-Bis(8-aza-7,7,8,9,9-pentamethyl-1,4-dioxa-spiro[4.5]-2-decylmethoxy)ethane
(IV-81) 1,4-Bis(8-aza-7,7,8,9,9-pentamethyl-1,4-dioxa-spiro[4.5]-2-decylmethoxy)-2-butene
(IV-82) 1,4-Bis(8-aza-7,7,8,9,9-pentamethyl-1,4-dioxa-spiro[4.5]-2-decylmethoxy)-2-butyne
(IV-83) α,α'-Bis(8-aza-7,7,8,9,9-pentamethyl-1,4-dioxaspiro[4.5]-2-decylmethoxy)-p-xylene
(IV-84) Bis(8-aza-7,7,8,9,9-pentamethyl-1,4-dioxaspiro[4.5]-2-decylmethyl)hexamethylene-1,6-dicarbamate
(IV-85) Bis(8-aza-7,7,8,9,9-pentamethyl-1,4-dioxaspiro[4.5]-2-decylmethyl)toluene-2,4-dicarbamate
(IV-86) Bis(8-aza-7,7,8,9,9-pentamethyl-1,4-dioxaspiro[4.5]-2-decylmethyl)diphenylmethane-p-p'-dicarbamate
(IV-87) Tris(8-aza-7,7,8,9,9-pentamethyl-1,4-dioxaspiro[4.5]-2-decylmethyl)trimeaate
(IV-88) Tris(8-aza-7,7,8,9,9-pentamethyl-1,4-dioxaspiro[4.5]-2-decylmethyl)phosphite
(IV-89) Tetrakis(8-aza-7,7,8,9,9-pentamethyl-1,4-dioxaspiro[4.5]-2-decylmethyl)pyromellitate
(IV-90) 8-Aza-7,7,9,9-tetramethyl-2-stearcyloxymethyl-1,4-dioxa-spiro[4.5]decane
(IV-91) 8-Aza-7,7,9,9-tetramethyl-2-(m-toluoyloxymethyl)-1,4-dioxa-spiro[4.5]decane
(IV-92) 8-Aza-7,7,9,9-tetramethyl-2-salicyloyloxymethyl)-1,4-dioxa-spiro[4.5]decane The compounds of the formula (V),
(V-1) Cis-2,4,7-trioxabicyclo[3.3.0]octane-3-spiro-4'-(2',2',6',6'-tetramethylpiperidine)
(V-2) Cis-2,4,7-trioxabicyclo[3.3.0]octane-3-spiro-4'-(1',2',2',6',6'-pentamethylpiperidine)
(V-3) Cis-2,4,7-trioxabicyclo[3.3.0]octane-3-spiro-4'-(1'-acetyl-2',2',6',6'-tetramethylpiperidine)

In this invention, the following are included as preferred compounds.

(a) Compounds having the aforementioned formula (II) wherein $R_1$ is hydrogen atom or methyl group, n is 1 or 2, $R_2$ is, when n is 1, a saturated aliphatic acyl group having carbon atoms of 2–18 or benzoyl group which may be substituted with alkyl of $C_1$–$C_4$ or hydroxy, preferably benzoyl or salicyloyl and, when n is 2, a saturated aliphatic diacyl group having carbon atoms of 4–12 or terephthaloyl group, and $R_5'$ is methyl group or ethyl group.

(b) Compounds having the aforementioned formula (III) wherein $R_1$ and $R_6$ are hydrogen atom, methyl group or allyl group.

(c) Compounds having the aforementioned formula (IV) wherein $R_1$ is hydrogen atom or methyl group, m is 1, n is 1 or 2, and $R_2$ is, when n is 1, a saturated aliphatic acyl group having carbon atoms of 2–18 or benzoyl group which may be substituted with alkyl of $C_1$–$C_4$ or hydroxy, preferably benzoyl or salicyloyl and, when n is 2, a saturated aliphatic diacyl group having carbon atoms of 4–12 or terephthaloyl.

The compounds of this invention may be prepared, for instance, as stated below, but the procedures per se may be effected in a well-known manner.

(1) The compounds (II-1), (III-1), (IV) and (V) can be prepared by reacting the triacetomamine derivatives (VI) with the trimethylol derivatives (VII), pentaerythritol (VIII), the glycerin derivatives (IX) and the meso-erythritol derivatives (X), respectively, in the presence of an acidic catalyst such as p-toluenesulfonic acid, sulfuric acid or hydrochloric acid is the presence or absence of a solvent with heating.

(a)
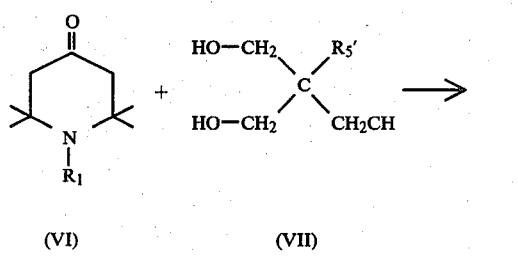

(VI) (VII)

(II-1)

(b)
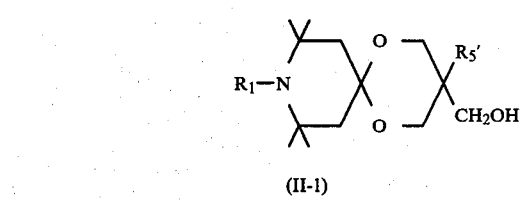

(VI) (VIII)

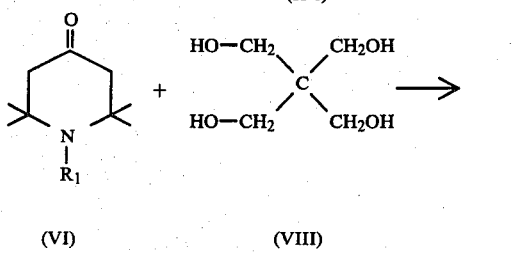

(III-1)

(c)
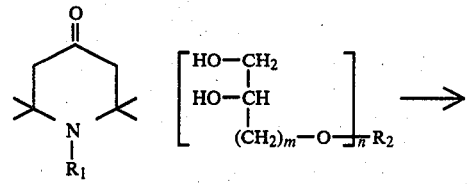

(VI) (IX)

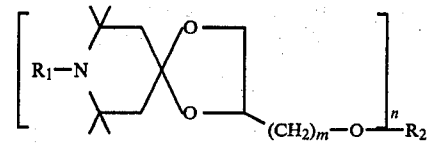

(IV)

(d)
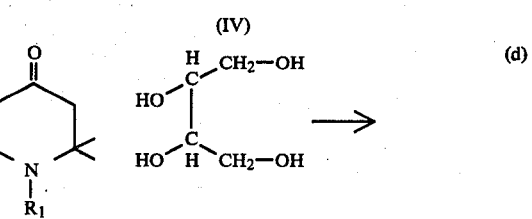

(VI) (X)

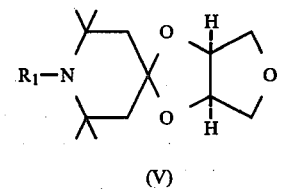

(V)

In the above formulae, $R_1$, $R_2$, $R'_5$, n and m are as defined above.

(2) Introduction of such groups as acyl group, alkyl group and the like into the hydroxyl group or the amine may be conducted by reacting with a halide in the presence of an acid-binding agent. In general, where the halide is employed in a small amount, the compound having the substituent introduced to the hydroxyl group is obtained, whereas the compound having the substituents introduced to the hydroxyl group and amine if used in an excess amount. As the acid-binding agent may be employed inorganic or organic basic substances such as sodium iodide, potassium carbonate, sodium hydroxide, sodium hydride, triethylamine, sodium alcoholate, potassium p-toluenesulfonate or sodium acetate. Alternatively, the introduction of acyl group may be effected through a reaction with an acid anhydride or an ester interchange reaction with an acid ester, instead of the above reaction with a halide.

(e)
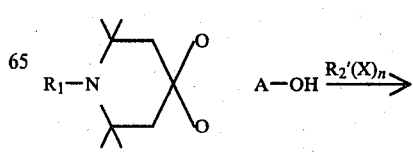

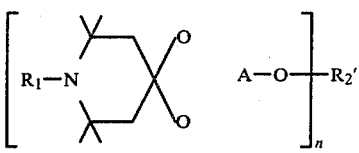

In the above formulae, $R_1$ and n are as defined above, $R'_2$ represents other group than hydrogen atom, N-substituted carbamoyl group, N-substituted thiocarbamoyl group or N-substituted dicarbamoyl group in the above $R_2$ and X represents halogen atom.

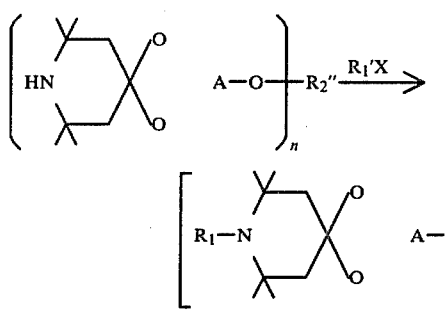

(f)

In the above formulae, A and n are as defined above, $R_1$ represents other group than hydrogen atom in the above $R_1$, $R''_2$ represents other group than hydrogen atom in the above $R_2$ and X represents halogen atom.

(3) Introduction of the N-substituted carbamoyl group, N-substituted thiocarbamoyl group into the hydroxyl group may be conducted through a reaction with a substituted isocyanic acid or a substituted isothiocyanic acid in the presence of an acid binding agent.

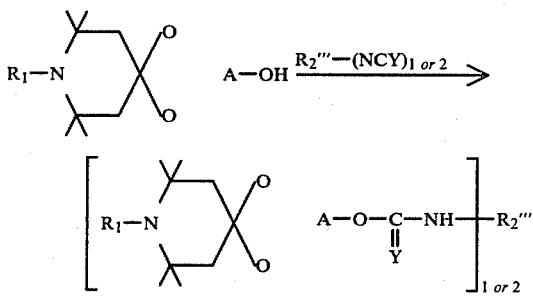

(g)

In the above formulae, A and $R_1$ are as defined above, X represents oxygen or sulfur atom, $R'''_2$ represents a substituent on the carbamoyl group or thiocarbamoyl group.

In this invention, the piperidine derivatives (I) employed as a stabilizer may be easily incorporated (I) employed as a stabilizer may be easily incorporated into a synthetic polymeric material by various methods commonly used in the art. The stabilizer may be added to a synthetic polymeric material at any stage in the manufacture of a molded product therefrom. For example, the stabilizer of a dry powder may be admixed with a synthetic polymeric material or a suspension or emulsion of the stabiliser may be admixed therewith.

The amount of the piperidine derivative (I) which may be added to a synthetic polymeric material according to this invention is varied upon the kind, nature and purpose for use of the synthetic polymeric material to be added. In general, the amount ranging in 0.01–5% by weight may be employed to the weight of a synthetic polymeric material, but a practical range may be varied upon the synthetic polymeric material and there may be used 0.01–2.0% by weight, desirably 0.02–1.0% by weight for polyolefin; 0.01–1.0% by weight, desirably 0.02–0.5% by weight for polyvinyl chloride and polyvinylidene chloride; 0.01–5.0% by weight, desirably 0.02–2.0% by weight for polyurethane polyamide.

The compounds according to the formulae (II) and (IV) of the present invention are excellent in compatibility in polymeric materials, especially polyolefin.

The above-mentioned stabilizer may be used alone or in admixture with known additives such as antioxidants, ultraviolet absorbents, fillers, pigments and the like. The additives are exemplified by the following.

Antioxidants

Simple 2,6-dialkylphenols, such as, for example, 2,6-di-tert.butyl-4-methylphenol, 2-tert.butyl-4,6-dimethylphenol, 2,6-di-tert.butyl-4-methoxymethylphenol and 2,6-dioctadecyl-4-methylphenol.

Derivatives of alkylated hydroquinones, such as, for example, 2,5-di-tert.butyl-hydroquinone, 2,5-di-tert.amyl-hydroquinone, 2,6-di-tert.butyl-hydroquinone, 2,5-di-tert.butyl-4-hydroxyanisole, 3,5-di-ter.butyl-4-hydroxyanisole and tris(3,5-di-tert.butyl-4-hydroxyphenyl)phosphite, 3,5-di-tert.butyl-4-hydroxyphenyl-stearate, di-(3-di-tert.butyl-4-hydroxyphenyl)adipate.

Hydroxylated thiodiphenyl ethers, such as, for example, 2,2'-thiobis(6-tert.butyl-4-methylphenol), 2,2'-thiobis(4-octylphenol), 4,4'-thiobis(6-tert.butyl-3-methyl-phenol), 4,4'-thiobis(3,6-di-sec.amylphenol) and 4,4'-thiobis (6-tert.butyl-2-methylphenol), 4,4'-Bis(2,6-dimethyl-4-hydroxyphenyl)disulfide.

Alkylidene-bisphenols, such as, for example, 2,2'-methylene-bis(6-tert.butyl-4-methylphenol), 2,2'-methylene-bis(6-tert.butyl-4-ethylphenol), 4,4'-methylenebis(6-tert.butyl-2-methylphenol), 4,4'-methylene-bis(2,6-di-tert.butylphenol), 2,6-di-(3-tert.butyl-5-methyl-2-hydroxybenzyl)-4-methylphenol, 2,2'-methylene-bis[4-methyl-6-(α-methylcyclohexyl)-phenol], 1,1-bis(3,5-dimethyl-2-hydroxyphenyl)-butane, 1,1-bis(5-tert.butyl-4-hydroxy-2-methylphenyl)-butane, 2,2-bis(5-tert.butyl-4-hydroxy-2-methylphenyl)butane, 2,2-bis(3,5-di-tert.butyl-4-hydroxyphenyl)propane, 1,1,3-tris-(5-tert.butyl-4-hydroxy-2-methylphenyl)butane, 2,2-bis(5-tert.butyl-4-hydroxy-2-methylphenyl)-4-m-dodecylmercaptobutane, 1,1,5,5-tetra(5-tert.butyl-4-hydroxy-2-methylphenyl)pentane and ethylene glycol bis[3,3-bis(3'-tert.butyl-4'-hydroxyphenyl)butyrate].

O-, N- and S-benzyl compounds, such as, for example, 3,5,3',5'-tetra-tert.butyl-4,4'-dihydroxydibenzylether, 4-hydroxy-3,5-dimethylbenzyl-mercaptoacetic acid octadecyl ester, tri(3,5-di-tert.butyl-4-hydroxybenzyl)amine, and bis(4-tert.butyl-3-hydroxy-2,6-dimethylbenzyl)dithiol-terephthalate.

Hydroxybenzylated malonic esters, such as, for example, 2,2-bis(3,5-di-tert.butyl-2-hydroxybenzyl)malonic acid dioctadecyl ester, 2-(3-tert.butyl-4-hydroxy-5-methylbenzyl)malonic acid dioctadecyl ester, 2,2-bis(3,5-ditert.butyl-4-hydroxybenzyl)malonic acid didodecylmercaptoethyl ester and 2,2-bis(3,5-di-tert.butyl-4-hydroxybenzyl)malonic acid di(4-tert.octylphenyl)ester.

Hydroxybenzyl-aromatics, such as, for example, 1,3,5-tri(3,5-di-tert.butyl-4-hydroxybenzyl)-2,4,6-trimethylbenzene, 1,4-di(3,5-di-tert.butyl-4-hydroxybenzyl)-2,3,5,6-tetramethylbenzene and 2,4,6-tri(3,5-di-tert.butyl-4-hydroxybenzyl)phenol.

s-Triazine compounds, such as, for example, 2,4-bisoctylmercapto-6-(3,5-di-tert.butyl-4-hydroxyanilino)-s-triazine, 2-octylmercapto-4,6-bis(3,5-di-tert.butyl-4-hydroxyanilino)-s-triazine, 2-octylmercapto-4,6-bis(3,5-di-tert.butyl-4-hydroxyphenoxy)-s-triaxine, 2,4,6-tris(3,5-ditert.butyl-4-hydroxyphenoxy)-s-triazine, 2,4,6-tris(3,5-di-tert.butyl-4-hydroxyphenylethyl)-s-triazine and 1,3,6-tris-(3,5-di-ter.butyl-4-hydroxybenzyl)isocyanurate.

Amides of 3,5-di-tert.butyl-4-hydroxyphenylpropionic acid, such as, for example, 1,3,5-tris(3,5-di-tert.butyl-4-hydroxyphenyl-propionyl)-hexahydro-s-triazine and N,N'-bis(3,5-di-tert.butyl-4-hydroxyphenyl-propionyl)hexamethylenediamine.

Esters of 3,5-di-tert.butyl-4-hydroxyphenylpropionic acid with monohydric or polyhydric alcohols, such as, for example, methanol, ethanol, octadecanol, 1,6-hexanediol; 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]-octane.

Esters of 5-tert.butyl-4-hydroxy-3-methylphenylpropionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentacrythritol, 3-thia-undecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

Esters of 3,5-di-tert.butyl-4-hydroxyphenylacetic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]octane.

Acylaminophenols, such as, for example, N-(3,5-di-tert.butyl-4-hydroxyphenyl)stearic acid amide and N,N'-bis(3,5-di-tert.butyl-4-hydroxyphenyl)-thio-bis-acetamide.

Benzylphosphonates, such as, for example, 3,5-di-tert.butyl-4-hydroxybenzylphosphonic acid di-methyl ester, 3,5-di-tert.butyl-4-hydroxybenzylphosphonic acid diethyl ester, 3,5-di-tert.butyl-4-hydroxybenzylphosphonic acid dioctadecyl ester and 5-tert.butyl-4-hydroxy-3-methylbenzylphosphonic acid dioctadecyl ester.

Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, mono- and di-octyliminodibenzyl and polymerized 2,2,4-trimethyl-1,2-dihydroquinoline.

UV-absorbers and light protection agents 2-(2'-Hydroxyphenyl)-benztriazoles, such as, for example, the 5'-methyl-, 3',5'-di-tert.butyl-, 5'-tert.butyl-, 5'-(1,1,3,3-tetramethyl-butyl)-, 5-chloro-3',5'-di-tert.butyl-, 5-chloro-3'-tert.butyl-5'-methyl-, 3'-sec.butyl-5'-tert.butyl-, 3'-[α-methylbenzyl]-5'-methyl-, 3'-[α-methylbenzyl]-5'-methyl-5-chloro-, 4'-hydroxy-; 4'-methoxy-, 4'-octoxy-, 3',5'-di-tert.amyl-, 3'-methyl-5'-carbomethoxyethyl-, 5-chloro-3',5'-di-tert.-amyl-derivatives.

2,4-Bis(2'-hydroxyphenyl)-6-alkyl-s-triazines, such as, for example, the 6-ethyl-, 6-undecyl- or 6-heptadecyl-derivatives.

2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivatives.

1,3-Bis(2'-hydroxy-benzoyl)benzenes, such as, for example, 1,3-bis(2'-hydroxy-4'-hexyloxy-benzoyl)-benzene, 1,3-bis(2'-hydroxy-4'-octoxy-benzoyl)-benzene, 1,3-bis(2'-hydroxy-4'-dodecyloxy-benzoyl)-benzene.

Esters of optionally substituted benzoic acids, such as, for example, phenyl salicylate, octylphenyl salicylate, di-benzoylresorcinol, bis(4-tert.butylbenzoyl)resorcinol, benzoyl-resorcinol, 3,5-di-tert.butyl-4-hydroxybenzoic acid 2,4-di-tert.butylphenyl ester, octadecyl ester or 2-methyl-4,6-di-tert.butylphenyl ester.

Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methylindoline.

Nickel compounds, such as, for example, nickel complexes of 2,2'-thiobis(4-tert.octylphenol), such as the 1:1 and 1:2 complex, optionally with other ligands such as n-butylamine, triethanolamine or N-cyclohexyl-diethanolamine, nickel complexes of bis(4-tert.octylphenyl)-sulphone, such as the 2:1 complex, optionally with other ligands such as 2-ethyl-caproic acid, nickel dibutyldithiocarbamate, nickel salts of 4-hydroxy-3,5-di-tert.butylbenzylphosphonic acid monoalkyl esters, such as the methyl, ethyl or butyl ester, the nickel complex of 2-hydroxy-4-methyl-phenyl-undecyl-ketopoxime and nickel 3,5-di-tert.butyl-4-hydroxybenzoate.

Oxalic acid dinmides, such as, for example, 4,4'-dioctyloxyoxanilide, 2,2'-dioctyloxy-5,5'-tert.butyloxanilide, 2,2'-di-dodecyloxy-5,5'-di-tert.butyloxanilide, 2-ethoxy-5-tert.butyl-2'-ethyl-oxanilide, 2-ethoxy-2'-ethyl-oxanilide, N,N'-bis-(3-dimethylaminopropyl)oxalamide, mixtures of o- and p-methoxy and o- and p-ethoxy-di-substituted oxanilides and mixtures of 2-ethoxy-5-tert.butyl-2'-ethoxanilide with 2-ethoxy-2'-ethyl-5,4'-di-tert.butyloxanilide.

Metal deactivators, such as, for example, oxanilide, isophthalic acid dihydrazide, sebacic acid bis-phenylhydrazido, bis-benzylidene oxalic acid di-hydrazide, N,N'-diacetyl-adipic acid dihydrazide, N,N'-bis-salicyloyloxalic acid dihydrazide, N,N'-bis-salicyloyl-hydrazine and N,N'-bis-(3,5-di-tert.butyl-4-hydroxyphenyl-propionyl)-hydrazine.

Phosphites, such as, for example triphenylphosphite, di-phenyl alkyl-phosphites, phenyl dialkylphosphites, trinonylphenylphosphite, trilaurylphosphite, trioctadecylphosphite, 3,9-di-isodecyloxy-2,4,8,10-tetraoxa-3,9-diphospha-spiro[5.5]undecane and tris(4-hydroxy-3,5-di-tert.butylphenyl)phosphite.

Compounds which destroy noroxide, such as, for example esters of β-thiodipropionic acid, e.g., the lauryl, stearyl, myristyl or tridecyl ester, salts of 2-mercaptobenzimidazole, e.g., the zinc salt, and diphenylthiourea.

Polyamide stabilizers, such as, for example, copper salts in combination with iodides and/or phosphorus compounds and salts of divalent manganese.

Basic co-stabilizers, such as, for example, polyvinylpyrrolidone, melamine, benzoguanamine, triallyl cyanurate, dicyandiamide, urea derivatives, hydrazine derivatives, amines, polyamides, polyurethanes and alkali metal salts and alkaline earth metal salts of higher saturated or unsaturated fatty acids, e.g., Ca stearate, Mg laurate, Ma ricinoleate, K palmitate and Zn stearate.

PVC stabilizers, such as, for example, organic tin compounds, organic lead compounds and Ba/Cd salts of fatty acids.

Nucleating agents, such as, for example, 4-tert.butylbenzoic acid, adipic acid and diphenylacetic acid.

Other additives, such as, for example, plasticizers, lubricants, e.g., glycerine monostearate, emulsifiers, antistatic agents, flameproofing agents, pigments, carbon black, asbestos, glass fibres, kaolin and talc.

Other additive such as these may be usually blended into the piperidine derivative (I) of this invention and advantageously employed at a ratio of 0.5-3 parts to 1 part.

Examples 1 to 8 describe the synthetic polymeric material compositions having incorporated therein the piperidine derivative (I) and their stabilizing effects and Referential Examples 1 to 14 describe the preparation of the piperidine derivative (I).

EXAMPLE 1

Into 100 parts of polypropylene ["Noblen JHH-G", trade name, after twice recrystallizations from monochlorobenzene, available from Mitsui Toatsu Chemicals Inc.] was incorporated 0.25 part of the stabilizer of this invention. The resulting mixture was blended and molten. The molten mixture was molded into a sheet with a thickness of 0.5 mm. under heating and pressure.

The sheet was exposed to irradiation of ultraviolet ray at 45° C. in a Fade-Meter and the time when the sheet becomes brittle was measured.

The results are shown in Table 1.

EXAMPLE 2

Into 100 parts of high-density polyethylene ["Hi-Zex", trade name, available from Mitsui Toatsu Chemicals Inc., after twice recrystallizations from toluene] was incorporated 0.25 part of the stabilizer of this invention. The resulting mixture was blended and molten and molded into a sheet with a thickness of 0.5 mm. under heating and pressure.

The sheet was exposed to irradiation of ultraviolet ray at 45° C. in a Fade-Meter and the time when the sheet becomes brittle was measured.

The results are given in Table 1. The Nos. of stabilizers recited hereinafter are referred to hereinbefore.

Table 1

| Stabilizer No. | Polypropylene | High-density Polyethylene |
|---|---|---|
| II-2 | 620 hours | 1280 hours |
| II-3 | 700 | 1460 |
| II-4 | 680 | 1440 |
| II-5 | 760 | 1580 |
| II-7 | 880 | 1760 |
| II-8 | 820 | 1640 |
| II-10 | 860 | 1920 |
| II-14 | 720 | 1700 |
| II-15 | 880 | 1820 |
| II-20 | 640 | 1180 |
| II-21 | 680 | 1420 |
| II-22 | 660 | 1260 |
| II-25 | 820 | 1780 |
| II-28 | 840 | 1880 |
| II-30 | 700 | 1620 |
| II-32 | 860 | 1760 |
| II-33 | 880 | 1940 |
| II-40 | 500 | 940 |
| II-44 | 580 | 1060 |
| II-50 | 620 | 1160 |
| II-51 | 720 | 1480 |
| II-56 | 840 | 1620 |
| II-57 | 880 | 1680 |
| II-59 | 820 | 1760 |
| II-72 | 680 | 1240 |
| II-73 | 560 | 1160 |
| II-74 | 460 | 1080 |
| II-75 | 920 | 1480 |
| II-76 | 920 | 1700 |
| II-77 | 900 | 1520 |
| II-78 | 880 | 1640 |
| II-79 | 900 | 1820 |
| II-80 | 880 | 1500 |
| II-81 | 740 | 1460 |
| II-82 | 900 | 1780 |
| III-1 | 720 | 1540 |
| III-2 | 780 | 1640 |
| III-3 | 820 | 1780 |
| III-4 | 800 | 1720 |
| III-7 | 780 | 1680 |
| III-8 | 760 | 1620 |
| III-9 | 840 | 1760 |
| III-10 | 880 | 1880 |
| III-11 | 900 | 1880 |
| III-12 | 940 | 1960 |
| IV-1 | 620 | 1300 |
| IV-2 | 660 | 1380 |
| IV-4 | 720 | 1580 |
| IV-5 | 680 | 1520 |
| IV-8 | 640 | 1480 |
| IV-9 | 800 | 1780 |
| IV-10 | 580 | 1220 |
| IV-11 | 640 | 1360 |
| IV-14 | 720 | 1560 |
| IV-16 | 720 | 1520 |
| IV-17 | 740 | 1600 |
| IV-19 | 860 | 1840 |
| IV-20 | 760 | 1640 |
| IV-24 | 620 | 1100 |
| IV-25 | 800 | 1740 |
| IV-26 | 760 | 1600 |
| IV-27 | 600 | 1220 |
| IV-28 | 780 | 1720 |
| IV-37 | 720 | 1440 |
| IV-40 | 780 | 1780 |
| IV-41 | 700 | 1620 |
| IV-42 | 720 | 1600 |
| IV-43 | 600 | 1480 |
| IV-44 | 740 | 1780 |
| IV-45 | 800 | 1820 |
| IV-53 | 620 | 1240 |
| IV-54 | 680 | 1440 |
| IV-56 | 640 | 1280 |
| IV-59 | 700 | 1340 |
| IV-60 | 780 | 1520 |
| IV-62 | 640 | 1320 |
| IV-71 | 800 | 1860 |
| IV-72 | 880 | 2020 |
| IV-74 | 940 | 2200 |
| IV-76 | 740 | 1700 |
| IV-77 | 640 | 1420 |
| IV-90 | 580 | 1360 |
| IV-91 | 560 | 1480 |
| IV-92 | 700 | 1680 |
| V-1 | 620 | 1380 |
| V-2 | 640 | 1420 |
| Tinuvin 327* | 300 | 640 |
| None | 60 | 380 |

*Tinuvin 327: 2-(2-hydroxy-3,5-di-tert-butylphenyl)-6-chloro-1,2,3-triazol

EXAMPLE 3

Into 100 parts of polystyrene ["Styron", trade name, after recrystallization from a mixture of benzene with methanol, available from Asahi-Dow Limited.] was incorporated 0.25 part of the stabilizer of this invention. The resulting mixture was molded at 180° C. under pressure into a plate with a thickness of 1 mm.

The plate thus formed was subjected to the exposure of ultraviolet ray irradiation in a Fade-Meter at 45° C. for 500 hours. A test piece of the trented plate was tested for color-difference by means of a color-difference colorimeter according to the method prescribed in Japanese Industrial Standard "K-7103", and a change of the yellowness index of the plate was calculated according to the following equation:

$$\Delta YI = YI - YI_0$$

wherein $\Delta YI$ means a change of yellowness index, YI means a yellowness index after exposure and $YI_0$ means an initial yellowness index of a test piece.

The results are shown in Table 2.

Table 2

| Stabilizer No. | $YI_0$ | $\Delta YI$ |
|---|---|---|
| II-8 | 4.8 | +2.7 |
| II-59 | 4.7 | +2.8 |
| II-76 | 4.0 | +2.0 |
| II-77 | 3.9 | +2.3 |
| III-1 | 4.9 | +3.2 |
| III-7 | 4.1 | +2.1 |
| III-11 | 3.9 | +2.3 |
| IV-1 | 4.6 | +3.3 |
| IV-9 | 4.5 | +2.7 |
| IV-25 | 4.5 | +3.0 |
| IV-45 | 3.8 | +2.3 |
| IV-76 | 4.1 | +3.1 |
| IV-80 | 4.3 | +4.2 |
| IV-82 | 4.1 | +3.8 |
| Tinuvin P* | 4.9 | +4.7 |
| None | 4.7 | +16.3 |

*Tinuvin P: 2-(2-hydroxy-5-methyl)benzo-1,2,3-triazol

EXAMPLE 4

Into 100 parts of ABS resin ["Kane Ace B-12", trade name, available from Kanegafuchi Chemical Industries, Co., Ltd.] was incorporated 0.5 part of the stabilizer of this invention, the resulting mixture was kneaded on a kneading roll at 160° C. for 6 minutes and then molded into a sheet with a thickness of about 0.5 mm.

The sheet was treated in a sunshine weather-ometer for 50 hours and treated for retentions of ultimate elongation and of ultimate tensile strength as well as coloration degree were determined by a conventional method. The results are shown in Table 3.

Table 3

| Stabilizer No. | Retention of elongation | Retention of tensile strength |
|---|---|---|
| II-5 | 69% | 76% |
| II-59 | 73% | 81% |
| III-10 | 72 | 79 |
| III-12 | 77 | 82 |
| IV-9 | 74 | 75 |
| IV-41 | 75 | 79 |
| IV-72 | 77 | 80 |
| None | 53 | 69 |

EXAMPLE 5

Into 100 parts of 6-nylon resin ["CM1011", trade name, available from Toray Industries Inc.] was incorporated 0.25 part of the stabilizer of this invention. The resulting mixture was heated and melted and then molded into a film having a thickness of about 0.1 mm. under pressure by a conventional compression molding machine. The film thus formed was aged under the following aging condition and thereafter subjected to a tensile test to determine the retentions of tensile strength and elongation.

Aging conditions (1) Exposure to ultraviolet ray for 200 hours in a Fade-Meter at 45° C.

(2) Aging at 160° C. for 2 hours in a Geer's aging tester. The results are shown in Table 4.

Table 4

| | Fade-meter | | Gear's aging tester | |
|---|---|---|---|---|
| Stabilizer No. | Retention of elongation | Retention of tensile strength | Retention of elongation | Retention of tensile strength |
| II-8 | 69% | 72% | 71% | 68% |
| II-59 | 73% | 82% | 72% | 80% |
| III-1 | 72 | 74 | 70 | 72 |
| III-7 | 69 | 71 | 71 | 70 |
| III-12 | 78 | 84 | 76 | 82 |
| IV-17 | 68 | 70 | 73 | 70 |
| IV-26 | 71 | 75 | 75 | 71 |
| IV-76 | 76 | 78 | 78 | 73 |
| None | 19 | 50 | 18 | 53 |

EXAMPLE 6

Into 100 parts of polycaprolacetone type polyurethane ["E-5080", trade name, available from The Nippon Elastollan Industries Ltd.] was incorporated 0.5 part of the stabilizer of this invention. The resulting mixture was heated and melted and then molded into a sheet having a thickness of about 0.5 mm. The sheet thus formed was subjected to the exposure to ultraviolet ray in a Fade-Meter at 45° C. for 15 hours and then tested for the retentions of elongation and tensile strength.

The results are shown in Table 5.

Table 5

| Stabilizer No. | Retention of elongation | Retention of tensile strength |
|---|---|---|
| II-5 | 86% | 91% |
| III-4 | 91 | 93 |
| III-11 | 96 | 96 |
| IV-1 | 83 | 87 |
| IV-17 | 85 | 90 |
| IV-26 | 88 | 91 |
| IV-76 | 90 | 93 |
| None | 74 | 52 |

EXAMPLE 7

Into 100 parts of polyvinyl chloride ["Geon 103EP", trade name, available from The Nippon Zeon Co., Ltd.] were incorporated 3 parts of butyl tin maleate, 0.5 part of butyl stearate and 0.25 part of the stabilizer of this invention and the resulting mixture and kneaded for 5 minutes on a kneading roll at 180° C. and formed into a sheet with a thickness of 0.5 mm. The sheet was treated is a sunshine weather-ometer for 300 hours and then the discoloration thereof was observed.

The results are shown in Table 6.

Table 6

| Stabilizer No. | Discoloration |
| --- | --- |
| II-5 | Pale brown |
| III-7 | " |
| III-12 | " |
| IV-2 | " |
| IV-11 | " |
| IV-19 | Orange-yellow |
| IV-45 | Pale brown |
| IV-72 | " |
| None | Dark brown |

EXAMPLE 8

Into 100 parts of polyester resin ["Ester-G13", trade name, available from Mitsui Toatsu Chemicals, Inc.] were incorporated 1 part of benzoyl peroxide and 0.2 parts of the stabilizer. The resulting mixture was cured by pre-heating at 60° C. for 30 minutes and then heated at 100° C. for additional 1 hour to be formed into a plate with a thickness of 3 mm.

The plate thus formed was exposed to irradiation in the sunshine weather-ometer for 60 hours and the change of yellowness thereof was determined according to the same method as described in the above Example 3.

The results are shown in Table 7.

Table 7

| Stabilizer No. | $II_0$ | $\Delta YI$ |
| --- | --- | --- |
| II-8 | 2.2 | +7.7 |
| III-1 | 2.3 | +6.9 |
| III-11 | 2.3 | +6.8 |
| III-12 | 2.5 | +7.3 |
| IV-9 | 2.5 | +8.0 |
| IV-16 | 2.3 | +8.2 |
| IV-45 | 2.2 | +7.9 |
| IV-72 | 2.3 | +7.7 |
| None | 1.8 | +13.1 |

REFERENTIAL EXAMPLE 1

9-Aza-3-hydroxymethyl-3,8,8,10,10-pentamethyl-1,5-dioxa-spiro-[5.5]undecane (Illustrated compound II-2)

To 32.7 g. of p-toluenesulfonate of triacetonamine were added 12 g. of trimethylolethane, 1.5 g. of p-toluenesulfonic acid and 200 ml. of toluene and reflux with heating was conducted for 5 hours while the water formed was removed. After cooling, neutralization was made by the addition of an 30% aqueous solution of sodium hydroxide and separation of liquids was effected to recover a toluene layer, which was then washed with water, dried and concentrated under reduced pressure. Residual crystals were recrystallized from a mixed liquid of 1:1 of benzene-petroleum ether to give the end product as white crystals melting at 125°-126° C.

Analysis for $C_{14}H_{27}NO_3$ Calculated: C, 65.33%; E, 10.57%; N, 5.41%. Found: C, 65.12%; H, 10.47%; N, 5.47%.

REFERENTIAL EXAMPLE 2

9-Aza-3-ethyl-3-hydroxymethyl-8,8,10,10-tetramethyl-1,5-dioxa-spiro[5.5]undecane (Illustrated compound II-21)

In the substantially same manner as shown in the Referential Example 1, 32.7 g. of p-toluenesulfonate of triacetonamine, 13.4 g. of trimethylolpropane and 3 g. of p-toluenesulfonic acid were reacted and the aftertreatment was effected to give the end product as white crystals melting at 106°-107° C.

Analysis for $C_{15}H_{29}NO_3$ Calculated: C, 66.38%; K, 10.77%; N, 5.16%. Found: C, 66.43%; H, 10.83%; N, 5.24%.

REFERENTIAL EXAMPLE 3

2,2,6,6-Tetramethylpiperidine-4-spiro-2'(1',3'-dioxane)-5'-spiro-5''-(1''',3''-dioxane)-2''-spiro-4'''-(2''',2''',6''',6'''-tetramethylpiperidine) (Illustrated compound III-I)

163 g. of p-toluenesulfonate of triacetonamine, 17.6 g. of pentaerythritol and 3 g. of p-toluenesulfonic acid were reacted and treated in the same manner as shown in Referential Example 1 to give the end product as white crystals melting at 136.5°-137° C.

Analysis for $C_{23}H_{42}N_2O_4$ Calculated: C, 67.28%; H, 10.31%; N, 6.82%. Found: C, 66.98%; H, 10.28%; N, 6.76%.

REFERENTIAL EXAMPLE 4

8-Aza-2-hydroxymethyl-7,7,9,9-tetramethyl-1,4-dioxa-spiro-[4.5]decane (Illustrated compound IV-1)

To 12.4 g. of p-toluenesulfonate of triacetonamine were added 7 g. of glycerine, 1 g. of p-toluenesulfonic acid and 25 ml. of toluene and the mixture was reacted with heating at 110° C. for 1 hour. After cooling, crystalline mass separated was recovered by filtration, 7 g. of potassium carbonate and 25 ml. of ice-water were added and extraction with chloroform was done. The chloroform solution was concentrated after drying, the crystalline residue was recrystallized from ethanol to give the end product as white crystals melting at 139°-140° C.

Analysis for $C_{12}H_{23}NO_3$ Calculated: C, 62.85%; H, 10.11%; N, 6.11%. Found: C, 63.10%; H, 10.11%; N, 6.02%.

IR spectrum (Nujol mull): The absorption band of $\nu_{C=O}$ which was observed in the starting material disappeared and the absorption bands of $\nu_{C-O}$ 1050 cm$^{-1}$ and $\nu_{OH}$ 3270 cm$^{-1}$ were seen.

REFERENTIAL EXAMPLE 5

2-Acetoxymethyl-8-aza-7,7,9,9-tetramethyl-1,4-dioxa-spiro-[4,5]decane (Illustrated compound IV-8)

In the wholly same manner as in Referential Example 4, p-toluenesulfonate of triacetonamine was reacted with glycerine monoacetate to give the end product as colorless liquid of b.p. 128° C./2 mmHg.

Analysis for $C_{14}H_{25}NO_4$ Calculated: C, 61.96%; H, 9.29%; N, 5.16%. Found: C, 62.20%; H, 9.38%; N, 5.32%.

IR spectrum (liquid film): $\nu_{c=o}$ 1745 cm$^{-1}$, $\nu_{C-O}$ 1040 cm$^{-1}$ NMR spectrum (CCl$_4$ soln.): 5.6–6.5 $\tau$(5H, multiplet), 7.97 $\tau$(3H, singlet), 8.4–8.6 $\tau$(4H, broad doublet), 8.86 $\tau$(12H, singlet).

REFERENTIAL EXAMPLE 6

Cis-2,4,7-trioxabicyclo[3.3.0]octane-3-spiro-4'-(2',2',6',6'-tetramethylpiperidine) Illustrated compound V-1)

TO 21.4 g. of p-toluenesulfonate of triacetonamine were 10.2 g. of meso-erythritol, 2 g. of p-toluenesulfonic acid and 25 ml. of toluene, the reaction was effected with heating at 95°–100° C. for 2.5 hours and then under reflux for additional 6 hours. After cooling, crystalline mass separated was recovered by filtration, an 10% aqueous soution of sodium hydroxide was added thereto and crystalline mass was separated after dissolution. The crystalline mass was recovered by filtration and dissolved in n-hexane. Then, the solution is dried and allowed to stand under cooling to separate crystals, which were recovered by filtration to give the end product as white crystals melting at 87°–88° C.

Analysis for $C_{13}N_{23}NO_3$ Calculated: C, 64.70%; H, 9.61%; N, 5.80%. Found: C, 64.58%; B, 9.55%; N, 5.73%.

IR spectrum (Nujol mull): The absorption band of $\nu_{C=O}$ seen in the starting material disappeared. NMR spectrum (CDCl$_3$ soln.): 5.15–5.17 $\tau$(2H, multiplet, J=1 c/s), 5.94 $\tau$ (2H, doublet, J=11 c/s), 6.57 $\tau$ (2H, multiplet, J=11 c/s, J=1 c/s), 8.31 $\tau$ (4H, doublet), 8.48 $\tau$ (4H, doublet), 8.80 $\tau$ (12H, singlet).

Mass spectrum: M+ m/e 241 (Calculated Molecular Weight 241)

In accordance with the methods shown in Referential Examples 1 to 6, the following compounds were synthesised.

The compounds of the formula (II):
9-Aza-3-hydroxymethyl-3,8,8,9,10,10-hexamethyl-1,5-dioxaspiro[5.5]undecane. bp 152°–154° C./3 mmHg.
9-Aza-9-(p-chlorobenzyl)-3-hydroxymethyl-3,8,8,10,10-pentamethyl-1,5-dioxa-spiro[5.5]undecane, mp 143°–144° C.
9-Aza-3-ethyl-3-hydroxymethyl-8,8,10,10-tetramethyl-9-(p-methylbenzyl)-1,5-dioxa-spiro[5.5]undecane. mp 145.5°–146° C.
9-Aza-3-hydroxymethyl-3,8,8,10,10-pentamethyl-9-iodomethyl-1,5-dioxa-spiro[5.5]undecane. mp 216°–217° C. (decomp.)
9-Aza-9-benzyl-3-ethyl-3-hydroxymethyl-8,8,10,10-tetramethyl-1,5-dioxaspiro[5.5]undecane. mp 110°–113° C.

The compounds of the formula (III):
1,2,2,6,6-Pentamethylpiperidine-4-spiro-2'-(1',3'-dioxane)-5'-spiro-5''-(1'',3''-dioxane)-2''-spiro-4'''-(1''',2''',2''',6''',6'''-pentamethylpiperidine). mp 201.5°–203° C.
1-Benzyl-2,2,6,6-tetramethylpiperidine-4-spiro-2'-(1',3'-dioxane)-5'-spiro-5''-(1'',3''-dioxane)-2''-spiro-4'''-(1'''-benzyl-2''',2''',6''',6'''-tetramethylpiperidine). mp 211°–212° C.

The compounds of the formula (IV):
8-Aza-2-hydroxymethyl-7,7,8,9,9-pentamethyl-1,4-dioxaspiro[4.5]decane. mp 77° C.
8-Aza-8-benzyl-2-hydroxymethyl-7,7,9,9-tetramethyl-1,4-dioxa-spiro[4.5]decane. m. 93.5°–94.5° C.
2-Acetoxymethyl-8-aza-7,7,8,9,9-pentamethyl-1,4-dioxaspiro[4.5]decane. bp 123°–125° C./0.5 mmHg
2-Acetoxymethyl-8-aza-8-benzyl-7,7,9,9-tetramethyl-1,4-dioxa-spiro[4.5]decane. bp 152°–154° C./0.002 mmHg.
8-Aza-8-(2-hydroxyethyl)-2-hydroxymethyl-7,7,9,9-tetramethyl-1,4-dioxa-spiro[4.5]decane. mp 94°–95° C.
8-Acetyl-8-aza-2-hydroxymethyl-7,7,9,9-tetramethyl-1,4-dioxa-spiro[4.5]decane. mp 113°–114° C.

The compound of the formula (V).
Cis-2,4,7-trioxabicyclo[3.3.0]octane-3-spiro-4'-(1',2',2',6',6'-pentamethylpiperidine). mp 83°–84° C.

REFERENTIAL EXAMPLE 7

3-Acetoxymethyl-9-aza-3,8,8,10,10-pentamethyl-1,5-dioxa-spiro[5.5]undecane (Illustrated compound II-3)

To a solution of 20 g. of 9-aza-3-hydroxymethyl-3,8,8,10,10-pentamethyl-1,5-dioxa-spiro[5.5]undecane and 26 g. of triethylamine in 100 ml. of ether was added 20 g. of acetyl chloride under cooling to 5°–10° C.

After heating under reflux for 3 hours and cooling, an 10% aqueous solution of potassium carbonate was added and extraction with ether was done. The ether solution was dried and concentrated. The residue was recrystallized from ether to give the end product as white crystals melting at 95°–96° C.

Analysis for $C_{16}H_{29}NO_4$ Calculated: C, 64.18%; H, 9.76%; N, 4.68%. Found: C, 64.17%; H, 9.60%; N, 4.62%.

IR spectrum (Nujol mull): $\nu_{C=O}$ 1730 cm$^{-1}$

REFERENTIAL EXAMPLE 8

2-Acetoxymethyl-8-aza-7,7,9,9-tetramethyl-1,4-dioxa-spiro[4.5]decane (Illustrated compound IV-8)

To 15 g. of 8-aza-2-hydroxymethyl-7,7,9,9-tetramethyl-1,4-dioxa-spiro[4.5]decane were added 27 g. of acetic anhydride and 25 ml. of chloroform and dissolved with heating. The reaction was conducted at room temperature for 4 days to separate crystalline acetate of the end product. After recovery by filtration and washing with ether, to 8.7 g. of the crystal were added 7.2 g. of potassium carbonate, 10 g. of ice and 10 ml. of water and extraction with chloroform was done. The chloroform solution was washed with a saturated solution of sodium chloride in water, dried and the chloroform was distilled off. The liquid residue was subjected to distillation under reduced pressure to give the end product as colorless liquid of bp 112° C./1 mmHg, which was the same as obtained in Referential Example 5.

Analysis for $C_{14}H_{26}NO_4$ Calculated: C, 61.96%; H, 9.29%; N, 5.16%. Found: C, 61.82%; H, 9.19%; N, 5.05%.

IR spectrum (liquid film): Wholly identified with that of the product obtained in Referential Example 5.

REFERENTIAL EXAMPLE 9.

Bis(8-aza-7,7,9,9-tetramethyl-1,4-dioxa-spiro[4,5]-2-decylmethyl)terephthalate (Illustrated compound IV-26)

To 3 g. of 8-aza-2-hydroxymethyl-7,7,9,9-tetramethyl-1,4-dioxa-spiro[4.5]decane were added 1.3 g. of terephthaloyl chloride, 0.9 g. of potassium carbonate and 30 ml. of benzene and the reaction was effected by heating under reflux for 4 hours. After cooling, to the reaction liquid was added an 5% aqueous solution of potassium carbonate and extraction with chloroform was done. The chloroform solution was dried and concentrated. The residue was cooled and the separated crystals were recovered by filtration. The benzene solution of the crystal was poured into a silica gel column and from those fractions eluted from ethyl acetate was given the end product as white crystals melting at 134°–135° C.

Analysis for $C_{32}H_{48}N_2O_8$ Calculated: C, 65.28%; H, 8.22%; N, 4.76%. Found: C, 65.54%; H, 8.17%; N, 4.95%.

IR spectrum (Nujol mull): $\nu_{C=O}$ 1730 cm$^{-1}$

In accordance with the methods shown in the Referential Examples 7 to 9, the following compounds were synthesized.

The compounds of the formula (II):
3-Acetoxymethyl-9-aza-3,8,8,9,10,10-hexamethyl-1,5-dioxaspiro[5.5]undecane. mp 91°–92° C.
3-Acryloyloxymethyl-9-aza-3,8,8,10,10-pentamethyl-1,5-dioxa-spiro[5.5]undecane. mp 76°–79° C.
9-Aza-3-benzoyloxymethyl-3,8,8,10,10-pentamethyl-1,5-dioxa-spiro[5.5]undecane. mp 91°–92° C.
9-Aza-3,8,8,9,10,10-hexamethyl-1,5-dioxn-3-stearoyloxymethyl-spiro[5.5]undecane. mp 41°–42° C.
3-Acetoxymethyl-9-aza-3-ethyl-8,8,10,10-tetramethyl-1,5-dioxa-spiro[5.5]undecane. mp 52°–53° C.
9-Aza-3-ethyl-8,8,9,10,10-pentamethyl-1,5-dioxa-3-stearoyloxymethyl-spiro[5.5]undecane. mp 43°–44° C.
9-Aza-3,8,8,9,10,10-hexamethyl-1,5-dioxa-3-salicyloyloxymethyl-spiro[5.5]undecane. mp 69°–71° C.
9-Aza-3-ethyl-8,8,9,10,10-pentamethyl-1,5-dioxa-3-salicyloyloxymethyl-spiro[5.5]undecane. mp 117.5°–118.5° C.
Bis(9-aza-3,8,8,10,10-pentamethyl-1,5-dioxa-spiro[5.5]-3-undecylmethyl)adipate. mp 107°–108° C.
Bis(9-aza-3,8,8,10,10-pentamethyl-1,5-dioxa-spiro-[5.5]-3-undecylmethyl)terephthalate. mp 127.5°–128.5° C.
3-Acetoxymethyl-9-aza-9-benzyl-3-ethyl-8,8,10,10-tetramethyl-1,5-dioxa-spiro[5.5]undecane mp 86°–88° C.
9-Aza-3-ethyl-3-stearoyloxymethyl-8,8,10,10-tetramethyl-1,5-dioxa-spiro[5.5]undecane mp 50°–52° C.
9-Aza-3-benzoyloxymethyl-3-ethyl-8,8,10,10-tetramethyl-1,5-dioxa-spiro[5.5]undecane mp 84°–86° C.
9-Aza-3-benzoyloxymethyl-3-ethyl-8,8,9,10,10-pentamethyl-1,5-dioxa-spiro[5.5]undecane mp 84°–85° C.
9-Aza-3-ethyl-3-salicyloyloxymethyl-8,8,10,10-tetramethyl-1,5-dioxa-spiro[5.5]undecane mp 110°–111° C.
Bis(9-aza-3-ethyl-8,8,10,10-tetramethyl-1,5-dioxaspiro[5.5]-3-undecylmethyl)adipate mp 87°–88.5° C.
Bis(9-aza-3-ethyl-8,8,9,10,10-pentamethyl-1,5-dioxaspiro[5.5]-3-undecylmethyl)adipate mp 55.5°–57° C.
Bis(9-aza-3,8,8,9,10,10-hexamethyl-1,5-dioxa-spiro[5.5]-3-undecylmethyl)adipate mp 130°–132° C.
Bis(9-aza-3-ethyl-8,8,10,10-tetramethyl-1,5-dioxaspiro[5.5]-3-undecylmethyl) terephthalate mp 129° C.
Bis(9-aza-3-ethyl-8,8,9,10,10-pentamethyl-1,5-dioxaspiro[5.5]-3-undecylmethyl)terephthalate mp 138°–140° C.

The compounds of the formula (IV):
2-Acetoxymethyl-8-acetyl-8-aza-7,7,9,9-tetramethyl-1,4-dioxa-spiro[4.5]decane. bp 123°–128° C./0.0007 mmHg.
8-Aza-2-butyryloxymethyl-7,7,9,9-tetramethyl-1,4-dioxaspiro[4.5]undecane. bp 150°–151° C./4 mmHg
8-Aza-2-decanoyloxymethyl-7,7,9,9-tetramethyl-1,4-dioxaspiro[4.5]undecane. bp 190°–192° C./2 mmHg
8-Aza-7,7,8,9,9-pentamethyl-1,4-dioxa-2-salicyloyloxymethyl-spiro[4.5]undecane. bp 188°–190° C./0.002 mmHg
8-Aza-8-benzyl-7,7,9,9-tetramethyl-2-(m-toluoyloxymethyl)1,4-dioxa-spiro[4.5]decane. bp 220°–226° C./0.001 mmHg
8-Aza-2-(p-chlorobenzoyloxymethyl)-7,7,9,9-tetramethyl-1,4-dioxa-spiro[4.5]decane. bp 205°–207° C./2 mmHg
2-(o-Anisoyloxymethyl)-8-aza-7,7,9,9-tetramethyl-1,4-dioxa-spiro[4.5]decane. bp 215°–217° C./3 mmHg
2-(o-Anisoyloxymethyl)-8-aza-7,7,8,9,9-pentamethyl-1,4-dioxa-spiro[4.5]decane. bp 216°–223° C./1 mmHg
Bis(8-aza-7,7,9,9-tetramethyl-1,4-dioxa-spiro[4.5]-2-decylmethyl)adipate. bp >250° C./2 mmHg
Bis(8-aza-7,7,9,9-tetramethyl-1,4-dioxa-spiro[4.5]-2-decylmethyl)sebacate p-toluenesulfonate. bp 145°–147° C.
Bis(8-aza-7,7,9,9-tetramethyl-1,4-dioxa-spiro[4.5]2-decylmethyl)succinate. by >250° C./2 mmHg
8-Aza-7,7,9,9-tetramethyl-2-stearoyloxymethyl-1,4-dioxaspiro[45.]decane mp 32°–34° C.
8-Aza-7,7,8,9,9-pentamethyl-2-stearoyloxymethyl-1,4-dioxa-spiro[4.5]docane mp 30°–34° C.
8-Aza-7,7,9,9-tetramethyl-2-(m-toluoyloxymethyl)-1,4-dioxa-spiro[4.5]decane bp 200°–203° C./3 mmHg
8-Aza-7,7,9,9-tetramethyl-2-salicyloyloxymethyl)-1,4-dioxa-spiro[4.5]decane mp 35°–37° C.
8-Aza-2-benzoyloxymethyl-7,7,9,9-tetramethyl-1,4-dioxaspiro[4.5]decane bp 192°–194° C./3 mmHg
8-Aza-2-benzoyloxymethyl-7,7,8,9,9-pentamethyl-1,4-dioxaspiro[4.5]decane bp 189°–191° C./0.2 mmHg
Bis(8-aza-7,7,8,9,9-pentamethhyl-1,4-dioxa-spiro[4.5]-2-decylmethyl)terephthalate bp 147°–148° C.

REFERENTIAL EXAMPLE 10

9-Aza-3-ethoxymethoxymethyl-3,8,8,10,10-pentamethyl-1,5-dioxaspiro[5.5]undecane (Illustrated compound II-51)

To a solution of 5 g. of 9-aza-3-hydroxymethyl-3,8,8,10,10-pentamethyl-1,5-dioxa-spiro[5.5]undecane and 5 g. of chloromethyl ethyl ether in 60 ml. of ether was added 10 ml. of triethylamine at 5°–10° C. and the reaction was effected at room temperature for 1 hour and with heating under reflux for additional 3 hours. After cooling, 30 ml. of an 30% aqueous solution of potassium carbonate was added to the reaction liquid and extraction with ether was done. The ether solution was subjected to distillation under reduced pressure after drying to give the end product as colorless liquid boiling at 138°–140° C./3 mmHg.

Analysis for $C_{17}H_{33}NO_4$ Calculated: C, 64.75%; H, 10.54%; N, 4.44%. Found: C, 64.35%; H, 10.43%; N, 4.41%.

REFERENTIAL EXAMPLE 11

2-Allyloxymethyl-8-aza-7,7,9,9-tetramethyl-1,4-dioxaspiro[4.5]decane (Illustrated compound IV-59)

To a solution of 4.6 g. of 8-aza-2-hydroxymethyl-7,7,9,9-tetramethyl-1,4-dioxa-spiro[4.5]decane dissolved in 20 ml. of dimethylformamide was added 1.1 g. of a 50% dispersion of sodium hydride in 0.2 g. portions. After evolution of hydrogen ceases, the reaction was effected at room temperature for additonal 1 hour. To the solution was added 2.5 g. of allyl bromide under ice-cooling and the reaction was effected at room temperature for 1 hour and then at 45° C. for additional 1 hour. Then, the reaction mixture was poured into 60 g. of ice and extraction with ether was done. The ether solution was dried and subjected to distillation under reduced pressure to give the end product as colorless liquid boiling at 114° C./2 mmHg Analysis for $C_{15}H_{27}NO_3$ Calculated: C, 66.88%; H, 10.10%; N, 5.20%.

Found: C, 66.94%; H, 9.98%; N, 5.08%.

IR spectrum (liquid film): $\nu_{C=C}$ 1645 cm$^{-1}$

In accordance with the method described in Referential Examples 10 and 11, the following compounds were synthesized.

The compound of the formula (II),

9-Aza-3-benzyloxymethyl-3,8,8,9,10,10-hexamethyl-1,5-dioxa-spiro[5.5]undecone. bp 185°–187° C./0.8 mmHg The compound of the formula (IV), 8-Aza-2-(2,3-epoxypropyloxymethyl)-7,7,9,9-tetramethyl-1,4-dioxa-spiro[4.5]decane. bp 132°–135° C./0.003 mmHg 8-Aza-2-methoxymethyl-7,7,9,9-tetramethyl-1,4-dioxa-spiro[4.5]decane. bp 94°–95° C./2 mmHg 2-Allyloxymethyl-8-aza-7,7,8,9,9-pentamethyl-1,4-dioxaspiro[4.5]decane. bp 122°–124° C./1 mmHg 8-Aza-2-benzyloxymethyl-7,7,9,9-tetramethyl-1,4-dioxaspiro[4.5]decane. bp 168°–170° C./1 mmHg

REFERENTIAL EXAMPLE 12

2,2,6,6-Tetramethyl-1-octylpiperidine-4-spiro-2'-(1',3'-dioxane)-5'-spiro-5''-(1'',3''-dioxane)-2''-spiro-4'''-(2''',2''',6''',6'''-tetramethylpiperidine) (Illustrated compound III-3) and 2,2,6,6-tetramethyl-1-octylpiperidine-4-spiro-2'-(-1',3'-dioxane)-5'-spiro-5''-(1'',3''-dioxane)-2''-spiro-4'''-(2''',2''',6''',6'''-tetramethyl-1'''-octylpiperidine) (Illustrated compound III-4)

To 8.2 g. of 2,2,6,6-tetramethylpiperidine-4--spiro-2'-(1',3'-dioxane)-5'-spiro-5'-spiro-5''-(1'',3''-dioxane)-2''-spiro-4'''-(2''',2''',6''',6'''-tetramethylpiperidine) were added 8.5 g. of octyl acetate and heating was effected at 185°–190° C. with stirring for 7 hours. After completion of the reaction, the potassium carbonate was filtered off, to the filtrate were added an aqueous solution of sodium hydroxide and benzene, separation of liquid was made by shaking, the benzene layer was recovered, dried and concentrated. The residue was flown into a silica column and fractions from elution with benzene gave crystalline mass, which was recrystallised from petroleum ether to give the end product, the N,N'-dioctyl derivative as white crystals melting at 136°–137° C.

Analysis for $C_{39}H_{74}N_2O_4$ Calculated C, 73.76%; H, 11.75%; N, 4.41%. Found: C, 74.04%; H, 11.75%; N, 4.48%.

Then, fractions from elution with ether gave crystalline mass, which was recrystallized from petroleum ether to give the end product, the N-monooctyl derivative as white crystals melting at 104°–105.5° C.

Analysis for $C_{31}H_{36}N_2O_4$ Calculated: C, 71.21%; H, 11.18%; N, 5.36%. Found: C, 71.36%; H, 11.19%; N, 5.45%.

REFERENTIAL EXAMPLE 13

2-Acetoxymethyl-8-aza-8-ethoxycarbonylmethyl-7,7,9,9-tetramethyl-1,4-dioxa-spiro[4,5]decane (Illustrated compound IV-17)

To 4 g. of 2-acetoxymethyl-8-aza-7,7,9,9-tetramethyl-1,4-dioxa-spiro[4.5]decane were added 0.6 g. of sodium hydroxide, 0.3 g. of sodium iodide and 20 ml. of benzene and to the resulting suspension was added 3.7 g. of ethyl monobromoacetate at 10° C. The reaction was effected at room temperature and then at 50°–60° C. for additional 1 hour. After cooling, to the reaction liquid was added an 5% aqueous solution of potassium carbonate and extraction with benzene was done. The benzene solution was washed with a saturated solution of sodium chloride in water, dried and concentrated. The residue was chromatographed with a silica gel column, fractions from elution with a solvent of benzene:n-hexane:ethyl acetate=4:2:1 gave crystallize mass, which was then recrystallized from petroleum ether to give the end product as white crystals melting at 82°–83° C.

Analysis for $C_{18}H_{31}NO_6$ Calculated: C, 60.48%; H, 8.74%; N, 3.93%. Found: C, 60.20%; H, 8.65%; N, 3.66%.

IR spectrum (Nujol null): $\nu_{C=O}$ 1745, 1735 cm$^{-1}$

In accordance with the method described in Referential Examples 12 and 13, the following compounds were synthesized.

The compounds of the formula (II):

9-Aza-3-(2,3-epoxypropyloxymethyl)-3,8,8,9,10,10-hexamethyl-1,5-dioxa-spiro[5.5]undecane. bp 159°–160° C./1 mmHg 3-Acetoxymethyl-9-aza-9-(2,3-epoxypropyl)-3,8,8,10,10-pentamethyl-1,5-dioxa-spiro[5.5]undecane. mp 106°–107° C.

3-Acetoxymethyl-9-aza-9-benzyloxycarbonyl-3,8,8,10,10-pentamethyl-1,5-dioxa-spiro[5.5]undecane. mp 96.5°–97.5° C.

3-Acetoxymethyl-9-aza-3-ethyl-9-methoxycarbonylmethyl-8,8,10,10-tetramethyl-1,5-dioxa-spiro[5.5]undecane mp 65°–67.5° C.

The compounds of the formula (III).

1-(2-Hydroxyethyl)-2,2,6,6-tetramethylpiperidine-4-spiro-2'-(1',3'-dioxane)-5'-spior-5''-(1'',3''-dioxane)-2''-spiro-4'''-[1'''-(2-hydroxyethyl)-2''',2''',6''',6'''-tetramethylpiperidine]. mp 194°–195° C.

1-(2-Acetoxyethyl)-2,2,6,6-tetramethylpiperidine-4-spiro-2'-(1',3'-dioxane)-5'-spiro-5''-(1'',3''-dioxane)-2''-spiro-4'''-[1'''-(2-acetoxyethyl)-2''',2''',6''',6'''-tetramethylpiperidine]. mp 172°–183° C.

1-(2-Acryloyloxyethyl)-2,2,6,6-tetramethylpiperidine-4-spiro-2'-(1',3'-dioxane)-5'-spiro-5''-(1'',3''-dioxane)-2''-spiro-4'''-[1'''-(2-acryloyloxyethyl)-2''',2''',6''',6'''-tetramethylpiperidine]. mp 162°–163° C.

1-(2-Benzoyloxyethyl)-2,2,6,6-tetramethylpiperidine-4-spiro-2'-(1',3'-dioxane)-5'-spiro-5''-(1'',3''-dioxane)-2''-spiro-4'''-[1'''-(2-benxoyloxyethyl)-2''',2''',6''',6'''-tetramethylpiperidine]. mp 243°–245° C.

1-(2,5-Epoxypropyl)-2,2,6,6-tetramethylpiperidine-4-spiro-2'-(1',5'-dioxane)-5'-spiro5''-(1'',3''-dioxane)-2''-spiro-4'''-[1'''-(2,3-epoxypropyl)-2''',2''',6''',6'''-tetramethylpiperidine]. mp 157°–159° C.

2,2,6,6-Tetramethyl-1-(2-stearoyloxyethyl)piperidine-4-spiro-2'-(1',3'-dioxane)-5'-spiro-5''-(1'',3''-dioxane)-2''-spiro-4'''-[2''',2''',6''',6'''-tetramethyl-1'''-(2-stearoyloxyethyl)piperidine] mp 70°-72° C.

2,2,6,6-Tetramethyl-1-methoxycarbonylmethyl-piperidine-4-spiro-2'-(1',3'-dioxane)-5'-spiro-5''-(1'',3''-dioxan 2''-spiro-4'''-(2''',2''',6''',6'''-tetramethyl-1'''-methoxycarbonylmethylpiperidine) mp 165°-167° C.

1-Allyl-2,2,6,6-tetramethylpiperidine-4-spiro-2'-(-1',3'-dioxane)-5'-spiro-5''-(1'',3''-dioxane)-2''-spiro-4'''-(1'''-allyl-2''',2''',6''',6'''-tetramethylpiperidine) mp 158°-159° C.

The compounds of the formula (IV):

2-Acetoxymethyl-8-allyl-8-aza-7,7,9,9-tetramethyl-1,4-dioxa-spiro[4.5]decane. bp 150°-153° C./1 mmHg.

2-Acetoxymethyl-8-aza-8-benzyl-7,7,9,9-tetramethyl-1,4-dioxa-spiro[4.5]decane. bp 152°-154° C./0.002 mmHg 2-Acetoxymethyl-8-aza-8-(2,3-epoxypropyl)-7,7,9,9-tetramethyl-1,4-dioxa-spiro[4.5] decane. bp 162°-165° C./0.002 mmHg 2-Acetoxymethyl-8-aza-8-(2-hydroxyethyl)-7,7,9,9-tetramethyl-1,4-dioxa-spiro[4.5] decane. bp 154°-155° C./0.0008 mmHg 2-Acetoxymethyl-8-(2-acetoxyethyl)-8-aza-7,7,9,9-tetramethyl-1,4-dioxa-spiro[4.5]decane. bp 159°-162° C./0.0014 mmHg 2-Acetoxymethyl-8-aza-8-cyanomethyl-7,7,9,9-tetramethyl-1,4-dioxa-spiro[4.5]decane. mp 59°-60° C.

8-Aza-8-(2-benzoyloxyethyl)-2-benzoyloxymethyl-7,7,9,9-tetramethyl-1,4-dioxa-spiro[4.5] decane. mp 110°-111° C.

8-Aza-2-2-(p-chlorobenzoyloxymethyl)-7,7,9,9-tetramethyl-1,4-dioxa-8-(2-propynyl)-spiro[4.5] decane. mp 102°-103° C.

The compound of the formula (V):
Cis-2,4,7-trioxabicyclo[3.3.0]octane-3-spiro-4'-(1',2',2',6',6'-pentamethylpiperidine). mp 83°-84° C.

REFERENTIAL EXAMPLE 14

9-Aza-3-ethyl-8,8,9,10,10-pentamethyl-1,5-dioxa-3-phenylcarbamoyloxymethyl-spiro[5.5]undecane (Illustrated compound II-44)

To 3 g. of 9-aza-3-ethyl-3-hydroxymethyl-8,8,9,10,10-pentamethyl-1,5-dioxa-spiro[5.5]undecane were added 2 ml. of triethylamine and 30 ml. of benzene and to the solution was added with stirring a solution of 1.3 g. of phenyl isocyanate dissolved in 20 ml. of benzene. The reaction was effected with heating at 70°-75° C. for 4.5 hours. The reaction liquid was concentrated and the residual liquid was flown into a silica gel column. Elution with a mixed solvent of benzene-ether (1:1) gave crystallize mass, which was then recrystallized from petroleum ether to give the end product as white crystals melting at 94° C.

Analysis for $C_{23}H_{36}N_2O_4$ Calculated: C, 68.28%; H, 8.97%; N, 6.93%. Found: C, 68.39%; H, 8.88%; N, 6.85%.

In accordance with the method as shown in Referential Example 14, the following compounds were synthesized.

The compounds of the formula (IV):

8-Aza-2-ethylcarbamoyloxymethyl-7,7,8,9,9-pentamethyl-1,4-dioxa-spiro[4.5]decane. bp 156°-160° C./0.003 mmHg 8-Aza-7,7,8,9,9-pentamethyl-1,4-dioxa-2-phenylcarbamoyloxymethyl-spiro[4.5]decane. bp 170°-172° C./0.0004 mmHg

What we claim is:

1. A compound having the formula I

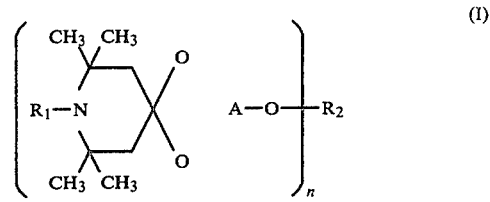

wherein,
R₁ represents hydrogen atom,
an alkyl group having 1 to 8 carbon atoms,
a substituted alkyl group having 1 to 3 carbon atoms in its alkyl moiety and selected from the group consisting of
a hydroxyalkyl,
an alkoxyalkyl having 1 to 4 carbon atoms in its alkoxy portion,
an alkanoyloxyalkyl having 2 to 18 carbon atoms in its alkanoyl portion,
an alkenoyloxyalkyl having 3 or 4 carbon atoms in its alkenoyl portion,
a benzoyloxyalkyl,
a cyanoalkyl,
a halogenoalkyl,
an epoxyalkyl, and
an alkoxycarbonylalkyl having 1 to 4 carbon atoms in its alkoxy portion,
an alkenyl group having 3 or 4 carbon atoms,
an alkynyl group having 3 or 4 carbon atoms,
benzyl group,
a benzyl group substituted with a halogen atom or a methyl group,
an alkanoyl or alkenoyl group, each having 2 to 8 carbon atoms,
an alkoxycarbonyl group having 2 to 5 carbon atoms or
benzoyloxycarbonyl group, n is the number 1 or 2,
R₂ represents, when n is 1, hydrogen atom,
an alkanoyl group having 1 to 18 carbon atoms and which may be interrupted in the alkyl portion by sulfur atom,
an alkenoyl group having 3 to 6 carbon atoms, each of which alkanoyl or alkenoyl groups may be substituted by phenyl or phenyl substituted with alkyl having 1 to 4 carbon atoms and/or hydroxy,
a benzoyl or naphthoyl group which may be substituted with an alkyl or alkoxy group having 1 to 4 carbon atoms, a halogen atom or a hydroxy group,
furoyl group,
isonicotinoyl group,
nicotinoyl group,
morpholinocarbonyl group,
an alkyl group having 1 to 18 carbon atoms,
an alkynyl group having 3 or 4 carbon atoms,
benzyl group,
phenyl group,
a o-, m- or p-tolyl group,
a α- or β-naphthyl group, an alkoxyalkyl or alkoxysulfonylalkyl group having 1 to 4 carbon atoms both in the alkyl and alkoxy portions, 2,3-epoxypropyl group, an N-substituted carbamoyl or thiocarbaboyl group wherein the substituent is an alkyl group having 1 to 4 carbon atoms, a phenyl group or a cyclohexyl group, a group derived from benzenesulfinic, benzenesulfonic, methanesulfonic, p-toluenesulfonic, diphenylphosphoric, $C_{1-8}$ dialkylphosphoric, diphenylphosphorus or $C_{1-8}$ dialkylphosphorus acid by removing a hydroxy group, or a group

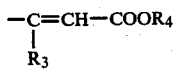

in which $R_3$ represents a hydrogen atom, an alkyl group having 1 to 4 carbon atoms or phenyl, and $R_4$ represents an alkyl group having 1 to 8 carbon atoms, when n is 2, $R_2$ represents carbonyl group, a saturated aliphatic diacyl group having 2 to 18 carbon atoms derived from a saturated dicarboxylic acid and which may be interrupted in the alkylene chain by sulfur atom, an unsaturated aliphatic diacyl group having 4 to 6 carbon atoms derived from an unsaturated dicarboxylic acid, terephthaloyl or isophthaloyl group, an alkylene group having 2 to 6 carbon atoms, an alkylene group having 4 to 6 carbon atoms, an alkenylene group having 4 to 6 carbon atoms, p-xylylene group, an N-substituted dicarbamoyl group wherein the N-substituent is alkylene having 1 to 6 carbon atoms, phenylene, tolylene or methanediphenylene group, or a group derived from sulfurous, sulfuric or phenylphosphorus acid by removing two hydroxy groups, A represents a group

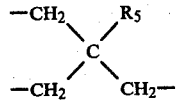

or a group

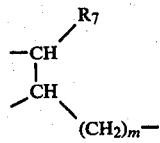

wherein $R_5$ represents hydrogen atom or an alkyl group having 1 to 3 carbon atoms, m is a number 1 or 2, and $R_7$ represents hydrogen atom.

2. A compound as claimed in claim 1, wherein $R_1$ is hydrogen atom, an alkyl group having 1 to 4 carbon atoms, allyl group, benzyl group, an alkoxycarbonylmethyl group having 1 to 4 carbon atoms in its alkoxy portion, 2,3-epoxypropyl group, an alkanoyloxyethyl group having 2 to 18 carbon atoms in the alkanoyl portion or an alkenoyloxyethyl group having 3 or 4 carbon atoms in the alkenoyl portion.

3. A compound as claimed in claim 1 wherein $R_1$ is hydrogen atom or methyl group.

4. A compound as claimed in claim 1 wherein $R_2$ represents, when n is 1, hydrogen atom, an alkanoyl group having 2 to 18 carbon atoms, benzoyl group, a benzoyl group substituted with an alkyl having 1 to 4 carbon atoms or hydroxy, an alkyl group having 1 to 18 carbon atoms, an allyl group or 2,3-epoxypropyl group, and when n is 2, a saturated aliphatic diacyl group having 4 to 12 carbon atoms derived from a saturated dicarboxylic acid or terephthaloyl group.

5. A compound as claimed in claim 1 wherein A represents a group

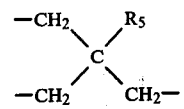

in which $R_5$ is methyl or ethyl group.

6. A compound as claimed in claim 5 wherein $R_1$ represents hydrogen atom or methyl group, $R_2$ represents, when n is 1, an alkanoyl group having 2 to 18 carbon atoms, benzoyl group or a benzoyl group substituted with an alkyl having 1 to 4 carbon atoms or hydroxy, and when n is 2, a saturated aliphatic diacyl group having 4 to 12 carbon atoms derived from a saturated dicarboxylic acid or terephthaloyl group, and $R_5$ represents methyl or ethyl group.

7. A compound as claimed in claim 6 wherein said compound is selected from the group consisting of, 9-aza-3-ethyl-8,8,9,10, 10-pentamethyl-1,5-dioxa-3-stearoyloxymethyl-spiro[5.5]undecane, 9-aza-3-ethyl-3-stearoyloxymethyl-8,8,10,10-tetramethyl-1,5-dioxa-spiro[5.5]undecane, 9-aza-3-benzoyloxymethyl-3-ethyl-8,8,10,10-tetramethyl-1,5-dioxa-spiro[5.5]undecane, 9-aza-3-benzoyloxymethyl-3-ethyl-8,8,9,10,10-pentamethyl-1,5-dioxa-spiro[5.5]undecane, 9-aza-3,8,8,9,10,10-hexamethyl-1,5-dioxa-3-salicyloyloxymethyl-spiro[5.5]undecane, 9-aza-3-ethyl-8,8,9,10,10-pentamethyl-1,5-dioxa-3-salicyloyloxymethyl-spiro[5.5]undecane, 9-aza-3-ethyl-3-salicyloyloxymethyl-8,8,10,10-tetramethyl-1,5-dioxa-spiro[5.5]undecane, bis(9-aza-3,8,8,10,10-pentamethyl-1,5-dioxa-spiro[5.5]-3-undecylmethyl)adipate, bis(9-aza-3,8,8,9,10,10-hexamethyl-1,5-dioxa-spiro[5.5]-3-undecylmethyl)adipate, bis(9-aza-3-ethyl-8,8,10,10-tetramethyl-1,5-dioxa-spiro[5.5]-3-undecylmethyl)adipate, bis(9-aza-3-ethyl-8,8,9,10,10-pentamethyl-1,5-dioxa-spiro[5.5]-3-undecylmethyl)adipate, bis(9-aza-3-ethyl-8,8,10,10-tetramethyl-1,5-dioxa-spiro[5.5]-3-undecylmethyl)terephthalate, and, bis(9-aza-3-ethyl-8,8,9,10,10-pentamethyl-1,5-dioxa-spiro[5.5]-3-undecylmethyl)terephthalate.

8. A compound as claimed in claim 1 wherein A represents a group

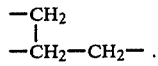

9. A compound as claimed in claim 8 wherein $R_1$ represents hydrogen atom or methyl group, and $R_2$ represents, when n is 1, an alkanoyl group having 2 to 18 carbon atoms, benzoyl group or a benzoyl group substituted with an alkyl having 1 to 4 carbon atoms or hydroxy, and when n is 2, a saturated aliphatic diacyl group having 4 to 12 carbon atoms derived from a saturated dicarboxylic acid or terephthaloyl group.

10. A compound as claimed in claim 9 wherein said compound is selected from the group consisting of, 8-aza-7,7,9,9-tetramethyl-2-stearoyloxymethyl-1,4-dioxa-spiro[4.5]decane,
8-aza-7,7,8,9,9-pentamethyl-1,4-dioxa-2-stearoyloxymethyl-spiro[4.5]decane,
8-aza-2-benzoyloxymethyl-7,7,9,9-tetramethyl-1,4-dioxa-spiro[4.5]decane,
8-aza-2-benzoyloxymethyl-7,7,8,9,9-pentamethyl-1,4-dioxa-spiro[4.5]decane,
8-aza-7,7,8,9,9-pentamethyl-1,4-dioxa-2-salicyloyloxymethyl-spiro[4.5]decane,
bis(8-aza-7,7,9,9-tetramethyl-1,4-dioxa-spiro[4.5]-2-decylmethyl)terephthalate, and,
bis(8-aza-7,7,8,9,9-pentamethyl-1,4-dioxa-spiro[4.5]-2-decylmethyl)terephthalate.

* * * * *